(12) United States Patent
Satish et al.

(10) Patent No.: US 12,207,924 B2
(45) Date of Patent: Jan. 28, 2025

(54) SYSTEMS AND METHODS FOR ASSESSING FLUIDS FROM A PATIENT

(71) Applicant: Stryker Corporation, Portage, MI (US)

(72) Inventors: Siddarth Satish, Portola Valley, CA (US); Peter Hyoung, Elmhurst, IL (US); Kevin J. Miller, Mountain View, CA (US); Andrew Hosford, Idaho Falls, ID (US); Eric Hsieh, Sunnyvale, CA (US)

(73) Assignee: Stryker Corporation, Portage, MI (US)

( * ) Notice: Subject to any disclaimer, the term of this patent is extended or adjusted under 35 U.S.C. 154(b) by 0 days.

(21) Appl. No.: 18/045,532

(22) Filed: Oct. 11, 2022

(65) Prior Publication Data

US 2023/0110782 A1 Apr. 13, 2023

Related U.S. Application Data

(63) Continuation of application No. 15/154,917, filed on May 13, 2016, now Pat. No. 11,504,037.
(Continued)

(51) Int. Cl.
*A61B 5/15* (2006.01)
*A61B 5/00* (2006.01)
(Continued)

(52) U.S. Cl.
CPC ........ *A61B 5/150221* (2013.01); *A61B 5/004* (2013.01); *A61B 5/02042* (2013.01);
(Continued)

(58) Field of Classification Search
None
See application file for complete search history.

(56) References Cited

U.S. PATENT DOCUMENTS

| 2,707,955 A | 5/1955 | Borden |
| 3,182,252 A | 5/1965 | Den Berg |

(Continued)

FOREIGN PATENT DOCUMENTS

| CA | 2870635 A1 | 10/2013 |
| CN | 101505813 A | 8/2009 |

(Continued)

OTHER PUBLICATIONS

"European Application Serial No. 12810640.8, Extended European Search Report dated Apr. 1, 2015", 8 pgs.
(Continued)

*Primary Examiner* — Jay B Shah
(74) *Attorney, Agent, or Firm* — Howard & Howard Attorneys PLLC

(57) ABSTRACT

Systems and methods for assessing a flow of fluids suctioned from a patient. The flow of fluids may be divided according to a flow division ratio. An image of a first portion of the fluids may be evaluated to determine an estimated blood component quantity as a representative fraction of the flow of fluids. An intermittent estimate of blood loss may be determined based on the flow division ratio and the estimated blood component quantity, and a total estimate of blood loss updated based on the intermittent estimate. The representative fraction is projected or extended to be an estimated blood component quantity of the second portion of the fluids that bypasses the receptacle. The images may be continuously captured with a camera, and a fluid level of the fluids with a receptable may be continuously monitored. The total estimate of blood loss may be displayed in real-time on a display.

18 Claims, 11 Drawing Sheets

Related U.S. Application Data

(60) Provisional application No. 62/162,117, filed on May 15, 2015.

(51) Int. Cl.
   *A61B 5/02* (2006.01)
   *A61B 5/103* (2006.01)
   *A61B 5/1455* (2006.01)

(52) U.S. Cl.
   CPC ........ *A61B 5/1032* (2013.01); *A61B 5/14551* (2013.01); *A61B 5/150099* (2013.01); *A61B 5/14552* (2013.01); *A61B 5/7435* (2013.01)

(56) References Cited

U.S. PATENT DOCUMENTS

| | | |
|---|---|---|
| 3,199,507 A | 8/1965 | Kamm |
| 3,367,431 A | 2/1968 | Baker |
| 3,646,938 A | 3/1972 | Haswell |
| 3,687,209 A | 8/1972 | Goldberg |
| 3,832,135 A | 8/1974 | Chlupsa et al. |
| 3,863,724 A | 2/1975 | Dalia, Jr. |
| 3,864,571 A | 2/1975 | Stillman et al. |
| 3,948,390 A | 4/1976 | Ferreri |
| 4,105,019 A | 8/1978 | Haswell |
| 4,149,537 A | 4/1979 | Haswell |
| 4,244,369 A | 1/1981 | McAvinn et al. |
| 4,402,373 A | 9/1983 | Comeau |
| 4,422,548 A | 12/1983 | Cheesman et al. |
| 4,429,789 A | 2/1984 | Puckett |
| 4,512,431 A | 4/1985 | Bloomfield |
| 4,562,842 A | 1/1986 | Morfeld et al. |
| 4,583,546 A | 4/1986 | Garde |
| 4,642,089 A | 2/1987 | Zupkas et al. |
| 4,681,571 A | 7/1987 | Nehring |
| 4,773,423 A | 9/1988 | Hakky |
| 4,784,267 A | 11/1988 | Gessler et al. |
| 4,832,198 A | 5/1989 | Alikhan |
| 4,917,694 A | 4/1990 | Jessup |
| 4,922,922 A | 5/1990 | Pollock et al. |
| 4,961,533 A | 10/1990 | Teller et al. |
| 5,014,798 A | 5/1991 | Glynn |
| 5,029,584 A | 7/1991 | Smith |
| 5,031,642 A | 7/1991 | Nosek |
| 5,048,683 A | 9/1991 | Westlake |
| 5,119,814 A | 6/1992 | Minnich |
| 5,119,830 A | 6/1992 | Davis |
| 5,128,036 A | 7/1992 | Svensson |
| 5,132,087 A | 7/1992 | Manion et al. |
| 5,190,059 A | 3/1993 | Fabian et al. |
| 5,231,032 A | 7/1993 | Ludvigsen |
| 5,236,664 A | 8/1993 | Ludvigsen |
| 5,285,682 A | 2/1994 | Micklish |
| 5,348,533 A | 9/1994 | Papillon |
| 5,369,713 A | 11/1994 | Schwartz et al. |
| 5,458,566 A | 10/1995 | Herrig et al. |
| 5,492,537 A | 2/1996 | Vancaillie |
| 5,522,805 A | 6/1996 | Vancaillie et al. |
| 5,568,262 A | 10/1996 | LaChapelle et al. |
| 5,595,456 A | 1/1997 | Berg et al. |
| 5,629,498 A | 5/1997 | Pollock et al. |
| 5,633,166 A | 5/1997 | Westgard et al. |
| 5,646,788 A | 7/1997 | Bietry |
| 5,650,596 A | 7/1997 | Morris et al. |
| 5,709,670 A | 1/1998 | Vancaillie et al. |
| 5,774,865 A | 6/1998 | Glynn |
| 5,807,358 A | 9/1998 | Herweck et al. |
| 5,851,835 A | 12/1998 | Groner |
| 5,923,001 A | 7/1999 | Morris et al. |
| 5,931,824 A | 8/1999 | Stewart et al. |
| 5,944,668 A | 8/1999 | Vancaillie et al. |
| 5,956,130 A | 9/1999 | Vancaillie et al. |
| 5,971,948 A | 10/1999 | Pages et al. |
| 5,984,893 A | 11/1999 | Ward |
| 5,996,889 A | 12/1999 | Fuchs et al. |
| 6,006,119 A | 12/1999 | Soller et al. |
| 6,061,583 A | 5/2000 | Ishihara et al. |
| 6,294,999 B1 | 9/2001 | Yarin |
| 6,359,683 B1 | 3/2002 | Berndt |
| 6,510,330 B1 | 1/2003 | Enejder |
| 6,641,039 B2 | 11/2003 | Southard |
| 6,699,231 B1 | 3/2004 | Sterman |
| 6,704,500 B2 | 3/2004 | Takematsu |
| 6,728,561 B2 | 4/2004 | Smith et al. |
| 6,730,054 B2 | 5/2004 | Pierce et al. |
| 6,777,623 B2 | 8/2004 | Ballard |
| 6,998,541 B2 | 2/2006 | Morris et al. |
| 7,001,366 B2 | 2/2006 | Ballard |
| 7,112,273 B2 | 9/2006 | Weigel et al. |
| 7,147,626 B2 | 12/2006 | Goodman et al. |
| 7,158,030 B2 | 1/2007 | Chung |
| 7,180,014 B2 | 2/2007 | Farber et al. |
| 7,274,947 B2 | 9/2007 | Koo et al. |
| 7,297,834 B1 | 11/2007 | Shapiro |
| 7,299,981 B2 | 11/2007 | Hickle et al. |
| 7,364,545 B2 | 4/2008 | Klein |
| 7,384,399 B2 | 6/2008 | Ghajar |
| 7,430,047 B2 | 9/2008 | Budd et al. |
| 7,430,478 B2 | 9/2008 | Fletcher-Haynes et al. |
| 7,469,727 B2 | 12/2008 | Marshall |
| 7,499,581 B2 | 3/2009 | Tribble et al. |
| 7,557,710 B2 | 7/2009 | Sanchez et al. |
| 7,641,612 B1 | 1/2010 | McCall |
| D611,731 S | 3/2010 | Levine |
| 7,670,289 B1 | 3/2010 | McCall |
| 7,703,674 B2 | 4/2010 | Stewart et al. |
| 7,708,700 B2 | 5/2010 | Ghajar |
| 7,711,403 B2 | 5/2010 | Jay et al. |
| 7,749,217 B2 | 7/2010 | Podhajsky |
| 7,795,491 B2 | 9/2010 | Stewart et al. |
| 7,819,818 B2 | 10/2010 | Ghajar |
| 7,909,806 B2 | 3/2011 | Goodman et al. |
| 7,966,269 B2 | 6/2011 | Bauer et al. |
| 7,995,816 B2 | 8/2011 | Roger et al. |
| 8,025,173 B2 | 9/2011 | Michaels |
| 8,105,296 B2 | 1/2012 | Morris et al. |
| 8,181,860 B2 | 5/2012 | Fleck et al. |
| 8,194,235 B2 | 6/2012 | Kosaka et al. |
| 8,241,238 B2 | 8/2012 | Hiruma |
| 8,279,068 B2 | 10/2012 | Morris et al. |
| 8,398,546 B2 | 3/2013 | Pacione et al. |
| 8,472,693 B2 | 6/2013 | Davis et al. |
| 8,479,989 B2 | 7/2013 | Fleck et al. |
| 8,576,076 B2 | 11/2013 | Morris et al. |
| 8,626,268 B2 | 1/2014 | Adler et al. |
| 8,693,753 B2 | 4/2014 | Nakamura |
| 8,704,178 B1 | 4/2014 | Pollock et al. |
| 8,792,693 B2 | 7/2014 | Satish et al. |
| 8,797,439 B1 | 8/2014 | Coley et al. |
| 8,897,523 B2 | 11/2014 | Satish et al. |
| 8,983,167 B2 | 3/2015 | Satish et al. |
| 9,047,663 B2 | 6/2015 | Satish et al. |
| 9,171,368 B2 | 10/2015 | Satish et al. |
| 9,595,104 B2 | 3/2017 | Satish et al. |
| 9,646,375 B2 | 5/2017 | Satish et al. |
| 9,652,655 B2 | 5/2017 | Satish et al. |
| 9,773,320 B2 | 9/2017 | Satish et al. |
| 9,824,441 B2 | 11/2017 | Satish et al. |
| 9,870,625 B2 | 1/2018 | Satish et al. |
| 9,936,906 B2 | 4/2018 | Satish et al. |
| 9,981,790 B1 | 5/2018 | Ost |
| 10,282,839 B2 | 5/2019 | Satish et al. |
| 10,424,060 B2 | 9/2019 | Satish et al. |
| 10,426,356 B2 | 10/2019 | Satish et al. |
| 10,528,782 B2 | 1/2020 | Satish et al. |
| 10,555,675 B2 | 2/2020 | Satish et al. |
| 10,641,644 B2 | 5/2020 | Satish et al. |
| 10,706,541 B2 | 7/2020 | Satish et al. |
| 10,789,710 B2 | 9/2020 | Satish et al. |
| 10,863,933 B2 | 12/2020 | Satish et al. |
| 10,957,179 B2 | 3/2021 | Satish et al. |
| 11,109,941 B2 | 9/2021 | Kumar et al. |
| 11,176,663 B2 | 11/2021 | Satish et al. |
| 11,504,037 B2 | 11/2022 | Satish et al. |

(56) References Cited

U.S. PATENT DOCUMENTS

| | | |
|---|---|---|
| 2002/0124017 A1 | 9/2002 | Mault |
| 2003/0069509 A1 | 4/2003 | Matzinger et al. |
| 2003/0095197 A1 | 5/2003 | Wheeler et al. |
| 2003/0130596 A1 | 7/2003 | Goltz |
| 2004/0031626 A1 | 2/2004 | Morris et al. |
| 2004/0129678 A1 | 7/2004 | Crowley et al. |
| 2005/0051466 A1 | 3/2005 | Carter et al. |
| 2005/0163354 A1 | 7/2005 | Ziegler |
| 2005/0209585 A1 | 9/2005 | Nord et al. |
| 2005/0265996 A1 | 12/2005 | Lentz |
| 2006/0058593 A1 | 3/2006 | Drinan et al. |
| 2006/0178578 A1 | 8/2006 | Tribble et al. |
| 2006/0224086 A1 | 10/2006 | Harty |
| 2006/0241453 A1 | 10/2006 | Nguyen-Dinh et al. |
| 2007/0004959 A1 | 1/2007 | Carrier et al. |
| 2007/0008622 A1 | 1/2007 | Sommer |
| 2007/0108129 A1 | 5/2007 | Mori |
| 2007/0243137 A1 | 10/2007 | Hainfeld |
| 2007/0287182 A1 | 12/2007 | Morris et al. |
| 2008/0029416 A1 | 2/2008 | Paxton |
| 2008/0030303 A1 | 2/2008 | Kobren et al. |
| 2008/0045845 A1 | 2/2008 | Pfeiffer et al. |
| 2008/0194906 A1 | 8/2008 | Mahony et al. |
| 2009/0076470 A1 | 3/2009 | Ryan |
| 2009/0257632 A1 | 10/2009 | Lalpuria et al. |
| 2009/0310123 A1 | 12/2009 | Thomson |
| 2009/0317002 A1 | 12/2009 | Dein |
| 2010/0003714 A1 | 1/2010 | Bachur, Jr. et al. |
| 2010/0007727 A1 | 1/2010 | Torre-Bueno |
| 2010/0025336 A1 | 2/2010 | Carter et al. |
| 2010/0027868 A1 | 2/2010 | Kosaka et al. |
| 2010/0066996 A1 | 3/2010 | Kosaka et al. |
| 2010/0087770 A1 | 4/2010 | Bock |
| 2010/0150759 A1 | 6/2010 | Mazur |
| 2010/0280117 A1 | 11/2010 | Patrick et al. |
| 2011/0066182 A1 | 3/2011 | Falus |
| 2011/0118647 A1 | 5/2011 | Paolini |
| 2011/0144595 A1 | 6/2011 | Cheng |
| 2011/0192745 A1 | 8/2011 | Min |
| 2011/0196321 A1 | 8/2011 | Wudyka |
| 2011/0200239 A1 | 8/2011 | Levine et al. |
| 2011/0275957 A1 | 11/2011 | Bhandari |
| 2011/0305376 A1 | 12/2011 | Neff |
| 2011/0316973 A1 | 12/2011 | Miller et al. |
| 2012/0000297 A1 | 1/2012 | Hashizume et al. |
| 2012/0064132 A1 | 3/2012 | Aizawa |
| 2012/0065482 A1 | 3/2012 | Robinson et al. |
| 2012/0127290 A1 | 5/2012 | Tojo et al. |
| 2012/0210778 A1 | 8/2012 | Palmer et al. |
| 2012/0257188 A1 | 10/2012 | Yan et al. |
| 2012/0262704 A1 | 10/2012 | Zahniser et al. |
| 2012/0271170 A1 | 10/2012 | Emelianov et al. |
| 2012/0309636 A1 | 12/2012 | Gibbons et al. |
| 2012/0327365 A1 | 12/2012 | Makihira |
| 2013/0010094 A1 | 1/2013 | Satish et al. |
| 2013/0094996 A1 | 4/2013 | Janssenswillen |
| 2013/0170729 A1 | 7/2013 | Wardlaw et al. |
| 2013/0245599 A1* | 9/2013 | Williams ............... A61M 1/77 604/113 |
| 2013/0301901 A1 | 11/2013 | Satish et al. |
| 2013/0303870 A1 | 11/2013 | Satish et al. |
| 2013/0305820 A1 | 11/2013 | Granstrand |
| 2013/0308852 A1 | 11/2013 | Hamsici et al. |
| 2014/0063180 A1 | 3/2014 | Sharma |
| 2014/0079297 A1 | 3/2014 | Tadayon et al. |
| 2014/0126788 A1* | 5/2014 | Satish ............... A61M 1/024 382/128 |
| 2014/0128838 A1 | 5/2014 | Satish |
| 2014/0207091 A1 | 7/2014 | Heagle et al. |
| 2014/0330094 A1 | 11/2014 | Pacione et al. |
| 2015/0294460 A1 | 10/2015 | Satish et al. |
| 2015/0294461 A1 | 10/2015 | Satish et al. |
| 2015/0310634 A1 | 10/2015 | Babcock et al. |
| 2015/0354780 A1 | 12/2015 | Wang |
| 2016/0015602 A1 | 1/2016 | Panzini |
| 2016/0027173 A1 | 1/2016 | Satish et al. |
| 2016/0123998 A1 | 5/2016 | MacIntyre et al. |
| 2016/0228639 A1 | 8/2016 | Zin |
| 2016/0243314 A1 | 8/2016 | Rodiera Olive |
| 2016/0327427 A1 | 11/2016 | Briones |
| 2016/0331282 A1 | 11/2016 | Satish et al. |
| 2017/0011276 A1 | 1/2017 | Mehring et al. |
| 2017/0023446 A1 | 1/2017 | Rietveld et al. |
| 2017/0184442 A1 | 6/2017 | Satish et al. |
| 2017/0185739 A1 | 6/2017 | Gomez et al. |
| 2017/0189621 A1 | 7/2017 | Olive |
| 2017/0351894 A1 | 12/2017 | Satish et al. |
| 2017/0352152 A1 | 12/2017 | Satish et al. |
| 2018/0104681 A1 | 4/2018 | Lee |
| 2018/0154088 A1 | 6/2018 | Broselow |
| 2018/0199827 A1 | 7/2018 | Satish et al. |
| 2019/0008427 A1 | 1/2019 | Satish et al. |
| 2020/0025822 A1 | 1/2020 | Rowell et al. |
| 2020/0104560 A1 | 4/2020 | Satish et al. |
| 2020/0113451 A1 | 4/2020 | Satish et al. |
| 2020/0232841 A1 | 7/2020 | Satish et al. |
| 2020/0311935 A1 | 10/2020 | Satish et al. |
| 2020/0380684 A1 | 12/2020 | Satish et al. |
| 2021/0059584 A1 | 3/2021 | Satish et al. |
| 2021/0192917 A1 | 6/2021 | Satish et al. |
| 2021/0236227 A1 | 8/2021 | Kumar et al. |
| 2021/0353383 A1 | 11/2021 | Kumar et al. |

FOREIGN PATENT DOCUMENTS

| | | |
|---|---|---|
| DE | 102009007733 A1 | 8/2010 |
| JP | S59161801 U | 10/1984 |
| JP | S61176357 A | 8/1986 |
| JP | S62144652 A | 6/1987 |
| JP | S62144652 U | 9/1987 |
| JP | H06510210 A | 11/1994 |
| JP | H07308312 A | 11/1995 |
| JP | H1137845 A | 2/1999 |
| JP | 2000227390 A | 8/2000 |
| JP | 2002331031 A | 11/2002 |
| JP | 2003075436 A | 3/2003 |
| JP | 2005052288 A | 3/2005 |
| JP | 3701031 B2 | 9/2005 |
| JP | 2006280445 A | 10/2006 |
| JP | 2008055142 A | 3/2008 |
| JP | 2008519604 A | 6/2008 |
| JP | 2009535639 A | 10/2009 |
| JP | 2010516429 A | 5/2010 |
| JP | 2011036371 A | 2/2011 |
| JP | 2011515681 A | 5/2011 |
| JP | 2011252804 A | 12/2011 |
| WO | 9217787 A1 | 10/1992 |
| WO | 9639927 A1 | 12/1996 |
| WO | 9710856 A1 | 3/1997 |
| WO | 2006053208 A1 | 5/2006 |
| WO | 2007129948 A1 | 11/2007 |
| WO | 2008094703 A2 | 8/2008 |
| WO | 2009117652 A1 | 9/2009 |
| WO | 2011019576 A1 | 2/2011 |
| WO | 2011145351 A1 | 11/2011 |
| WO | 2013009709 A2 | 1/2013 |
| WO | 2013172874 A1 | 11/2013 |
| WO | 2013173356 A1 | 11/2013 |
| WO | 2014013213 A1 | 1/2014 |
| WO | 2015161003 A1 | 10/2015 |
| WO | 2016187071 A1 | 11/2016 |
| WO | 2017111324 A1 | 6/2017 |
| WO | 2017112913 A1 | 6/2017 |
| WO | 2018125812 A1 | 7/2018 |
| WO | 2020069278 A1 | 4/2020 |
| WO | 2020081435 A1 | 4/2020 |
| WO | 2020247258 A1 | 12/2020 |
| WO | 2021003130 A1 | 1/2021 |

OTHER PUBLICATIONS

"European Application Serial No. 13790449.6, Extended European Search Report dated Nov. 17, 2015", 7 pgs.

(56) References Cited

OTHER PUBLICATIONS

"European Application Serial No. 16183350.4, Extended European Search Report dated Nov. 4, 2016", 8 pgs.
"International Application Serial No. PCT/US2012/045969, International Search Report dated Sep. 17, 2012", 2 pgs.
"International Application Serial No. PCT/US2013/021075, International Search Report dated Mar. 26, 2013", 2 pgs.
"International Application Serial No. PCT/US2013/040976, International Search Report dated Sep. 24, 2013", 2 pgs.
"Optimizing protocols in obstetrics", ACOG, Series 2, (2012), 25 pgs.
"U.S. Appl. No. 13/544,664, Final Office Action dated Feb. 12, 2016", 10 pgs.
"U.S. Appl. No. 13/894,054, Final Office Action dated Aug. 26, 2016", 7 pgs.
"U.S. Appl. No. 14/876,628, Final Office Action dated Jul. 26, 2016", 5 pgs.
ACOG (2012). "Optimizing protocols in obstetrics," Series 2, 25 total pages.
Adkins, A R, et al., "Accuracy of blood loss estimations among anesthesia providers", AANA Journal 82, (2014), 300-306.
Adkins, A.R. et al. (2014). "Accuracy of blood loss estimations among anesthesia providers," <i>AANA Journal </i>82 (4):300-306.
Aklilu, A, "Gauss Surgical Measures Blood Loss with a Smartphone", [Online]. Retrieved from the Internet: <http://www.health2con.com/news/2012/06/14/gauss-surgical-measures-blood-loss-with-a-smartphone>, (Jun. 14, 2012).
Aklilu, A. Gauss Surgical Measures Blood Loss with a Smartphone. Jun. 14, 2012.<http://www.health2con.com/news/2012/06/14/gauss-surgical-measures-blood-loss-with-a-smartphone/>, 6 pages.
Al-Kadri, H M, et al., "Effect of education and clinical assessment on the accuracy of postpartum blood loss estimation", BMC Preq. Childbirth 14, 110, 7 pgs.
Al-Kadri, H.M. et al. (2014). "Effect of education and clinical assessment on the accuracy of post partum blood loss estimation," <i>BMC Preg. Childbirth </i>14:110, 7 total pages.
AWHONN Practice Brief (2014). "Quantification of blood loss: AWHONN practice brief No. 1," <i>AWHONN </i>p. 1-3.
Bellad, et al., "Standardized Visual Estimation of Blood Loss during Vaginal Delivery with its Correlation Hematocrit Changes—A Descriptive Study", South Asian Federation of Obstetrics and Gynecology 1.1, (2009), 29-34.
Bellad, M.B. et al. (2009). "Standardized Visual Estimation of Blood Loss during Vaginal Delivery with Its Correlation Hematocrit Changes—A Descriptive Study." South Asian Federation of Obstetrics and Gynecology 1:29-34.
Bose, P, et al., "Improving the accuracy of estimated blood loss at obstetric haemorrhage using clinical reconstructions", BJOG 113(8), (2006), 919-924.
Bose, P. et al. (2006). "Improving the accuracy of estimated blood loss at obstetric haemorrhage using clinical reconstructions," <i>BJOG </i>113(8):919-924.
Eipe, N, et al., "Perioperative blood loss assessment—How accurate?", Indian J. Anaesth. 50(1), (2006), 35-38.
Eipe, N. et al. (2006). "Perioperative blood loss assessment—How accurate?" <i>Indian J. Anaesth</i>. 50(1):35-38.
Extended European Search Report dated Apr. 1, 2015, for EP Application No. 12 810 640.8, filed on Jul. 9, 2012, 8 pages.
Extended European Search Report dated Jul. 12, 2019, for EP Application No. 19 156 549.8, filed on Jul. 9, 2012, 8 pages.
Extended European Search Report dated Nov. 17, 2015, for EP Application No. 13 790 449.6, filed on Jan. 10, 2013, 8 pages.
Extended European Search Report dated Nov. 23, 2015, for EP Application No. 13 790 688.9, filed on May 14, 2013, 9 pages.
Extended European Search Report dated Nov. 4, 2016, for EP Application No. 16 183 350.4, filed on Jul. 9, 2012, 9 pages.
Extended European Search Report dated Sep. 18, 2017, for EP Application No. 15 780 590.4, filed on Apr. 15, 2015, 8 pages.
Final Office Action dated Aug. 26, 2016, for U.S. Appl. No. 13/894,054, filed May 14, 2013, 7 pages.
Final Office Action dated Feb. 12, 2016, for U.S. Appl. No. 13/544,664, filed Jul. 9, 2012, 9 pages.
Final Office Action dated Feb. 4, 2019, for U.S. Appl. No. 15/389,365, filed Dec. 22, 2016, 22 pages.
Final Office Action dated Jul. 26, 2016, for U.S. Appl. No. 14/876,628, filed Oct. 6, 2015, 5 pages.
Habak, P J, et al., "A comparison of visual estimate versus calculated estimate of blood loss at vaginal delivery", British J. Med. Medical Res. 11(4), (2016), 1-7.
Habak, P.J. et al. (2016). "A comparison of visual estimate versus calculated estimate of blood loss at vaginal delivery," <i>British J. Med. Medical Res</i>. 11(4):1-7.
Holmes, A A, et al., "Clinical evaluation of a novel system for monitoring surgical hemoglobin loss", Anesth. Analg. 119, (2014), 588-594.
Holmes, A.A. et al. (2014). "Clinical evaluation of a novel system for monitoring surgical hemoglobin loss," <i>Anesth. Analg</i>. 119(3):588-594.
International Search Report dated Aug. 18, 2016, for PCT Application No. PCT/US2016/032561, filed on May 13, 2016, 2 pages.
International Search Report dated Jul. 8, 2015, for PCT Application No. PCT/US2015/026042, filed on Apr. 15, 2015, 2 pages.
International Search Report dated Mar. 26, 2013, for PCT Application No. PCT/US2013/021075, filed on Jan. 10, 2013, 2 pages.
International Search Report dated Mar. 8, 2017, for PCT Application No. PCT/US2016/068452, filed on Dec. 22, 2016, 3 pages.
International Search Report dated Sep. 17, 2012, for PCT Application No. PCT/US2012/045969, filed on Jul. 9, 2012, 2 pages.
International Search Report dated Sep. 24, 2013, for PCT Application No. PCT/US2013/040976, filed on May 14, 2013, 2 pages.
Jones, R. (2015). "Quantitative measurement of blood loss during delivery," <i>AWHONN </i>p. S41.
Kamiyoshihara, M. et al. (2008). "The Utility of an Autologous Blood Salvage System in Emergency Thoracotomy for a Hemothorax After Chest Trauma," <i>Gen. Thorac. Cardiovasc. Surg</i>. 56:222.
Lyndon, A. et al. (2010). "Blood loss: Clinical techniques for ongoing quantitative measurement," <i>CMQCC Obstetric Hemorrhage Toolkit</i>, pp. 1-7.
Lyndon, A. et al. (2015). "Cumulative quantitative assessment of blood loss," <i>CMQCC Obstetric Hemorrhage Toolkit Version 2.0</i>, pp. 80-85.
Manikandan, D. et al. (2015). "Measurement of blood loss during adenotonsillectomy in children and factors affecting t," <i>Case Reports in Clinical Medicine </i>4:151-156.
Merck for Mother's Program (2012). Blood loss measurement: Technology opportunity assessment, 9 total pages.
Non-Final Office Action dated Apr. 11, 2018, for U.S. Appl. No. 15/416,986, filed Jan. 26, 2017, 6 pages.
Non-Final Office Action dated Apr. 20, 2017, for U.S. Appl. No. 13/894,054, filed May 14, 2013, 7 pages.
Non-Final Office Action dated Aug. 13, 2015, for U.S. Appl. No. 13/544,664, filed Jul. 9, 2012, 8 pages.
Non-Final Office Action dated Aug. 2, 2016, for U.S. Appl. No. 13/544,664, filed Jul. 9, 2012, 6 pages.
Non-Final Office Action dated Dec. 15, 2015, for U.S. Appl. No. 14/876,628, filed Oct. 6, 2015, 8 pages.
Non-Final Office Action dated Feb. 21, 2019, for U.S. Appl. No. 15/594,017, filed May 12, 2017, 23 pages.
Non-Final Office Action dated Jul. 13, 2018, for U.S. Appl. No. 15/389,365, filed Dec. 22, 2016, 14 pages.
Non-Final Office Action dated Mar. 20, 2015, for U.S. Appl. No. 14/613,807, filed Feb. 4, 2015, 8 pages.
Non-Final Office Action dated Mar. 24, 2017, for U.S. Appl. No. 14/687,862, filed Apr. 15, 2015, 22 pages.
Non-Final Office Action dated Mar. 30, 2016, for U.S. Appl. No. 13/894,054, filed May 14, 2013, 9 pages.
Non-Final Office Action dated May 9, 2014, for U.S. Appl. No. 13/544,679, filed Jul. 9, 2012, 7 pages.
Non-Final Office Action dated Sep. 5, 2014, for U.S. Appl. No. 13/738,919, filed Jan. 10, 2013, 8 pages.

(56) References Cited

OTHER PUBLICATIONS

Notice of Allowance dated Aug. 8, 2017, for U.S. Appl. No. 14/687,862, filed Apr. 15, 2015, 6 pages.
Notice of Allowance dated Feb. 15, 2017, for U.S. Appl. No. 13/544,664, filed Jul. 9, 2012, 10 pages.
Notice of Allowance dated Jun. 25, 2015, for U.S. Appl. No. 14/613,807, filed Feb. 4, 2015, 10 pages.
Notice of Allowance dated May 12, 2014, for U.S. Appl. No. 13/544,646, filed Jul. 9, 2012, 10 pages.
Notice of Allowance dated Nov. 10, 2014, for U.S. Appl. No. 13/738,919, filed Jan. 10, 2013, 10 pages.
Notice of Allowance dated Oct. 26, 2016, for U.S. Appl. No. 14/876,628, filed Oct. 6, 2015, 11 pages.
Notice of Allowance dated Sep. 3, 2014, for U.S. Appl. No. 13/544,679, filed Jul. 9, 2012, 8 pages.
Pogorelc, D. iPads in the OR: New Mobile Platform to Monitor Blood Loss During Surgery. MedCityNews, Jun. 6, 2012. http://medcitynews.com/2012/06/ipads-in-the-or-new-mobile-platform-to-monitor-blood-loss-during-surgery, 2 pages.
Roston, A.B. et al. (2012). "Chapter 9: Blood loss: Accuracy of visual estimation," in <i>A comprehensive textbook of postpartum hemorrhage: An essential clinical reference for effective management</i>, 2.SUP.nd .edition, Sapiens publishing, pp. 71-72.
Sant et al. (2012). "Exsanguinated Blood Volume Estimation Using Fractal Analysis of Digital Images," <i>Journal of Forensic Sciences </i>57:610-617.
Schorn, M.N. (2010). "Measurement of blood loss: Review of the literature," <i>J. Midwifery and Women's Health </i>55(1):20-27.
Sukprasert, M. et al. (2006). "Increase accuracy of visual estimation of blood loss from education programme," <i>J. Med. Assoc. Thai </i>89(suppl. 4):S54-S59.

U.S. Appl. No. 15/416,986, filed Jan. 26, 2017, by Satish et al.
U.S. Appl. No. 15/594,017, filed May 12, 2017, by Satish et al.
U.S. Appl. No. 15/943,561, filed Apr. 2, 2018, by Satish et al.
Written Opinion of the International Searching Authority dated Jul. 8, 2015, for PCT Application No. PCT/US2015/026042, filed on Apr. 15, 2015, 4 pages.
Written Opinion of the International Searching Authority dated Mar. 26, 2013, for PCT Application No. PCT/US2013/021075, filed on Jan. 10, 2013, 6 pages.
Written Opinion of the International Searching Authority dated Mar. 8, 2017, for PCT Application No. PCT/US2016/068452, filed on Dec. 22, 2016, 9 pages.
Written Opinion of the International Searching Authority dated Sep. 17, 2012, for PCT Application No. PCT/US2012/045969, filed on Jul. 9, 2012, 4 pages.
Written Opinion of the International Searching Authority dated Sep. 24, 2013, for PCT Application No. PCT/US2013/040976, filed on May 14, 2013, 4 pages.
Written Opinion of the International Searching Authority mailed on Aug. 18, 2016, for PCT Application No. PCT/US2016/032561, filed on May 13, 2016, 5 pages.
"European Application Serial No. 13790688.9, Extended European Search Report dated Nov. 23, 2015", 9 pgs.
"International Application Serial No. PCT/US2016/032561, International Preliminary Report on Patentability dated Nov. 30, 2017", 7 pgs.
"Quantification of blood loss: AWHONN practice brief No. 1", AWHONN Practice Brief, (2014), 1-3.
"U.S. Appl. No. 15/154,917, Decision on Appeal Brief mailed May 27, 2020", U.S. Appl. No. 15/154,917, 2 pgs.

\* cited by examiner

SYSTEMS AND METHODS FOR ASSESSING FLUIDS FROM A PATIENT

CROSS-REFERENCE TO RELATED APPLICATIONS

This is a continuation of co-pending U.S. application Ser. No. 15/154,917, filed May 13, 2016, which claims priority to U.S. Provisional Patent Application No. 62/162,117, filed on May 15, 2015, the entire contents of each being hereby incorporated by reference. The application is also related to International Application No. PCT/US2016/032561, filed May 13, 2016, the entire contents of which is hereby incorporated by reference.

BACKGROUND OF THE INVENTION

Inaccurate estimation of fluid loss (e.g., blood loss) from a patient, such as during a surgical procedure, may put the patient's health at risk. For example overestimation of patient blood loss results in the unnecessary consumption of transfusion-grade blood, and may lead to shortages of transfusion-grade blood that is needed for other patients. As another example, underestimation of patient blood loss may lead to delayed resuscitation and transfusion, increased risk of infections, tissue death, or even patient death, such as in the event of hemorrhage.

Furthermore, inaccurate estimation may be a significant contributor to high operating and surgical costs for hospitals, clinics, and other medical facilities. In particular, unnecessary blood transfusions, resulting from overestimation of patient blood loss, lead to higher operating costs for medical institutions. Additionally, delayed blood transfusions, resulting from underestimation of patient blood loss, have been associated with billions of dollars in avoidable patient infections and re-hospitalizations annually. Thus, it is desirable to have more accurate systems and methods for assessing fluids from a patient.

BRIEF SUMMARY OF THE INVENTION

Described herein are systems and methods for assessing fluids from a patient. Generally, a system for assessing fluids from a patient may be operated in a fill mode and a flush mode. The system may include a receptacle including an inlet port, an outlet port, and a third port; a valve system in fluidic communication with the receptacle; and one or more features in the receptacle to aid in optical imaging of fluids. In the fill mode, the valve system may direct suction from a vacuum source through the third port into the receptacle, thereby drawing fluid through the inlet port into the receptacle. Additionally, in the flush mode, the valve system may direct suction from the vacuum source through the outlet port, thereby drawing fluid through the outlet port out of the receptacle. The receptacle may further include a fourth port, such that in the fill mode the valve system directs suction from the vacuum source to a fluid retrieval device coupled to the inlet port and closes the fourth port. Conversely, in the flush mode, the valve system may open the fourth port.

The valve system may be configured to be automatically actuated or manually actuated. For example, in some variations, the system may include a controller configured to actuate the valve system to toggle between the fill mode and flush mode. The controller may be configured to actuate the valve system based on a fluid level signal indicating a volume of fluids detected in the receptacle. The system may include one or more sensors coupled to the receptacle and configured to detect the volume of fluids in the receptacle, and to generate a fluid level signal based on the detection of volume of fluids in the receptacle. More specifically, the system may include a first sensor configured to detect a high threshold volume of fluids in the receptacle, and/or a second sensor configured to detect a low threshold volume of fluids in the receptacle.

In some variations, the one or more features in the receptacle to aid optical imaging of fluids may include an insert that cooperates with a surface of the receptacle to define a region of substantially uniform thickness. The insert may be coupled to the receptacle or may be integrally formed with the receptacle. In other variations, the one or more features in the receptacle may include a surface of the receptacle that at least partially defines a region in which fluid has a color gradient. Furthermore, the system may include an optical fiducial on the receptacle.

Generally, a method for assessing fluids from a patient may use a receptacle including an inlet port, an outlet port, and a third port. The method may include collecting fluids from the patient in the receptacle by suctioning from a vacuum source through the third port of the receptacle to draw fluids through the inlet port into the receptacle, obtaining an image of the collected fluids with the aid of one or more features in the receptacle, and draining the collected fluids upon reaching a high threshold volume of fluids in the receptacle by suctioning from the vacuum source through the outlet port, thereby drawing fluids through the outlet port and out of the receptacle. The method may further include collecting fluids from the patient in the receptacle upon reaching a low threshold volume of fluids in the receptacle. In some variations, the receptacle may further include a fourth port, and the method may include closing the fourth port when collecting fluids and opening the fourth port when draining the collected fluids.

The method may include actuating a valve system to toggle between collecting fluids and draining fluids. In some variations, the method may include detecting the volume of fluids in the receptacle and generating a fluid level signal using one or more sensors based on the detection of volume of fluids in the receptacle. The valve system may be actuated based on the level signal indicating a volume of fluids detected in the receptacle.

The method may further include identifying a receptacle image region in the obtained image and determining one or more pixel color values of at least a portion of the receptacle image region. An estimated concentration of a blood component in the receptacle may be based on the one or more pixel color values. Furthermore, an estimated quantity of the blood component in the receptacle may be based on the estimated concentration of the blood component in the receptacle and an estimated volume of fluids in the receptacle.

BRIEF DESCRIPTION OF THE DRAWINGS

FIG. 4B is a cross-sectional view along line A-A of the exemplary receptacle shown in FIG. 4A.

DETAILED DESCRIPTION

Examples of various aspects and variations of the invention are described herein and illustrated in the accompanying drawings. The following description is not intended to limit the invention to these embodiments, but rather to enable a person skilled in the art to make and use this invention.

I. Systems and Methods Overview

Generally, the systems and methods described herein for assessing fluids from a patient are used to assess fluids that are lost by a patient during a surgical procedure. Images of the fluids may be intermittently generated and evaluated in order to assess the fluids. For example, the systems and methods described herein may be used to track or otherwise estimate, based at least in part on the images of fluid, a quantity of fluid (e.g., blood) lost by the patient during the surgical procedure and/or quantity of a blood component (e.g., hemoglobin). In other examples, the systems and methods may additionally or alternatively be used to track or otherwise assess total mass, total volume, and/or aggregate concentration of red blood cells, platelets, plasma, and/or other blood components lost by the patient during the surgical procedure. These assessments, and other fluid-related information described in further detail below, may be updated and displayed in substantially real-time during the surgical procedure and/or at the conclusion of the surgical procedure.

Figure 1:
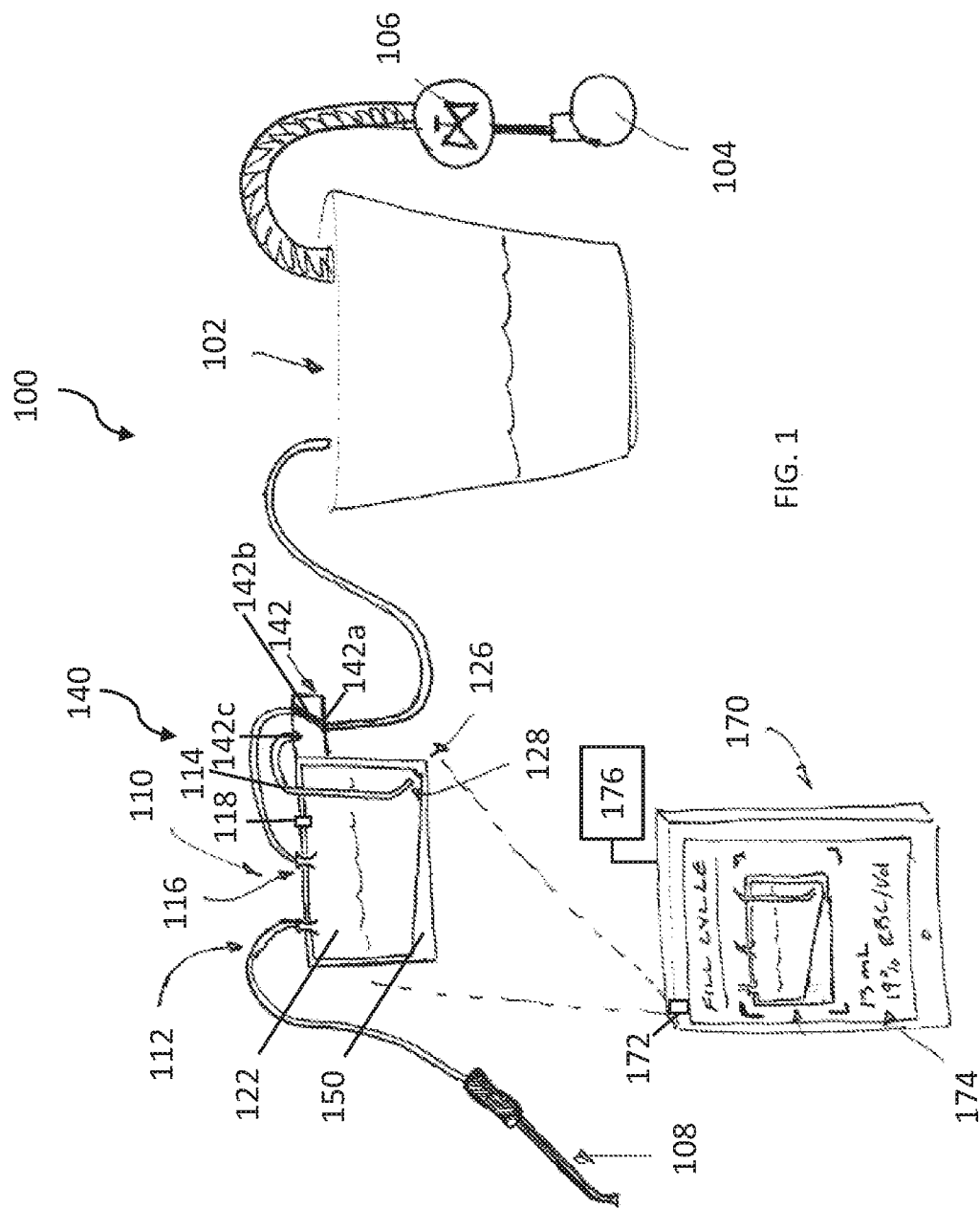
FIG. 1 is a schematic of one variation of the system for assessing fluids from a patient.

More specifically, during a surgical procedure, fluids lost by the patient may be collected and passed into a receptacle. In one variation, the system has a valve system that alternates between a fill mode in which the fluids accumulate in the receptacle and a flush mode in which accumulated fluids drain out of the receptacle (e.g., to a sealed waste management system). For example, as shown in FIG. 1, a fluid retrieval device 108 (e.g., suction wand) or other source of patient fluids may collect patient fluids from a surgical site, a canister, a surgical textile, and/or other fluid source containing fluids to be assessed. The collected patient fluids may be passed via tubing into a receptacle 110, and may continue to flow into a second receptacle 102 (e.g., canister or waste management system). In other words, the receptacle 110 may be placed in fluidic communication with the fluid retrieval device 108 (or other fluid source) and the second receptacle 102. In such an arrangement, the receptacle 110 receives and accumulates patient fluids from the fluid retrieval device 108 or other fluid source, allows the imaging of the accumulated patient fluids, and drains the patient fluids (e.g., into the second receptacle 102), in a repeatable cycle. Furthermore, the receptacle 110 and/or fluid retrieval device 108 may be in fluidic communication with one or more vacuum sources (e.g., a vacuum pump 104 associated with the second receptacle 102) configured to provide suction to the fluid retrieval device 108 for collecting fluids. Additionally, a filter for removing clot matter or other non-fluidic debris may be placed in the fluidic path between the fluid retrieval device and second receptacle. For example, this filter may, optionally, be included in the fluid retrieval device. In other examples, the filter may be incorporated in any suitable component in the fluidic path between the fluid retrieval device and the second receptacle. The one or more vacuum sources may additionally or alternatively be configured to provide suction for draining the receptacle 110. The systems described herein can be inserted into preexisting setups with waste management systems that collect patient fluids, without the need for extensive equipment additions or modifications.

The systems and methods described herein may be used in a variety of settings, including in a hospital or clinic setting (e.g., operating or clinic setting), a military setting (e.g., battlefield) or other suitable medical treatment settings. This information can be used to improve medical treatment of patients, as well as reduce costs to medical institutions and patients. For instance, medical practitioners (e.g., nurses, surgeons) who receive this information during and/or after a surgical procedure can then make appropriate decisions for treatment of the patient (such as determining whether to provide a blood transfusion to the patient and how much blood is necessary) based on more accurate information on patient status. In particular, with more accurate information on the patient fluid loss, practitioners can, for example, avoid providing unnecessary blood transfusions (which deplete inventory of blood transfusions and increase operating costs and medical bills), while also avoiding delayed blood transfusions (which would risk patient health).

II. Systems for Assessing Fluids from a Patient

Generally, a system for assessing fluids from a patient may have one or more components enabling a fill mode and a flush mode. In the fill mode, patient fluids are accumulated in the receptacle, while in the flush mode, the patient fluids are drained out of the receptacle. For instance, the system may have components that operate in the fill mode to accumulate patient fluids in the receptacle until the receptacle contains a predetermined threshold volume of fluid, upon which the components may operate in the flush mode to drain patient fluids from the receptacle. When another predetermined threshold volume of fluid remains in the reservoir (or when a predetermined threshold volume of fluid has been drained), the components again may operate in the fill mode to accumulate more patient fluids in the reservoir in another fill-flush cycle. In this manner, the components may toggle between the fill and flush modes to intermittently fill and empty the reservoir while the lost patient fluids continue to be collected and passed into the reservoir. Additionally, at one or more points in time while the patient fluids are in the receptacle (e.g., when a threshold volume of fluid has accumulated in the receptacle, before the system drains the patient fluids), a camera may generate one or more images of the fluid, which can be evaluated to assess fluid-related information.

As shown in FIG. 1, an example of a system 100 for assessing fluid from a patient may include a receptacle 110 including an inlet port 112, an outlet port 114, and a third port 116; a valve system 140 in fluidic communication with the receptacle; and one or more features 150 in the receptacle to aid in optical imaging of fluids. As described above, the system 100 may be operable in a fill mode and a flush mode. In the fill mode, the valve system 140 directs suction from a vacuum source 104 (associated with the second receptacle 102) through the third port 116 into the receptacle 110, where suction is communicated into the receptacle and through the inlet port 112, thereby drawing fluid through the inlet port 112 into the receptacle 110. In the flush mode, the valve system 140 directs suction from the vacuum source through the outlet port 114, thereby drawing fluid through the outlet port out of the receptacle. In some variations, as further described below, the valve system may be automatically actuated to toggle between the fill and flush modes, such as with a controller and sensor system, while in some variations the valve system may be additionally or alternatively manually actuated. Additionally, the system may further include a camera 172 configured to intermittently generate images of the fluid accumulated in the receptacle 110 (e.g., periodically or whenever the receptacle is sufficiently full) and/or a processor 176 configured to evaluate images of the fluid to estimate fluid-related information or other characterization of the fluid (e.g., estimate fluid volume, estimate concentration of a blood component, estimate quantity of the blood component, etc.). Furthermore, the system may include a display 174 configured to display the images of the fluid and/or at least some of the fluid-related information estimated by evaluation of the images.

The system may include one or more filters to remove clots, solids, and/or other non-fluidic debris out of the patient fluids. For instance, at least one filter may be placed in the fluidic path before the receptacle 110 (e.g., in the fluid retrieval device or in tubing between the fluid retrieval device and the receptacle), in the receptacle (e.g., coupled to the inlet port or outlet port), before one or more components of the valve system 140 (e.g., in tubing between the receptacle and the valve system), and/or before or in the second receptacle 102. However, one or more filters may be placed in any suitable location in the fluidic path between the fluid retrieval device and the second receptacle.

At least some of the electronic components of the system may be in an integrated device and placed near the patient during the surgical procedure (e.g., in the operating room) to assess patient fluids that are collected and passed through the receptacle. For instance, at least the camera, processor, and/or display may be combined in a handheld or mobile electronic computing device 170 (e.g., that executes a native fluid analysis application program). Such a handheld or mobile device may, for example, be a tablet computer, laptop computer, mobile smartphone, etc. which may include a camera 172, processor 176, and a display 174. However, in other variations some or all of these components may be separated as discrete interconnected devices. For example, the camera and display may be located substantially near the receptacle during the surgical procedure (e.g., in the operating room) while the processor may be located at a remote location (e.g., in the operating room separate from the camera and/or display, or outside the operating room), communicating with the camera and display through a wired or wireless connection or other network.

Receptacle

Figure 2:
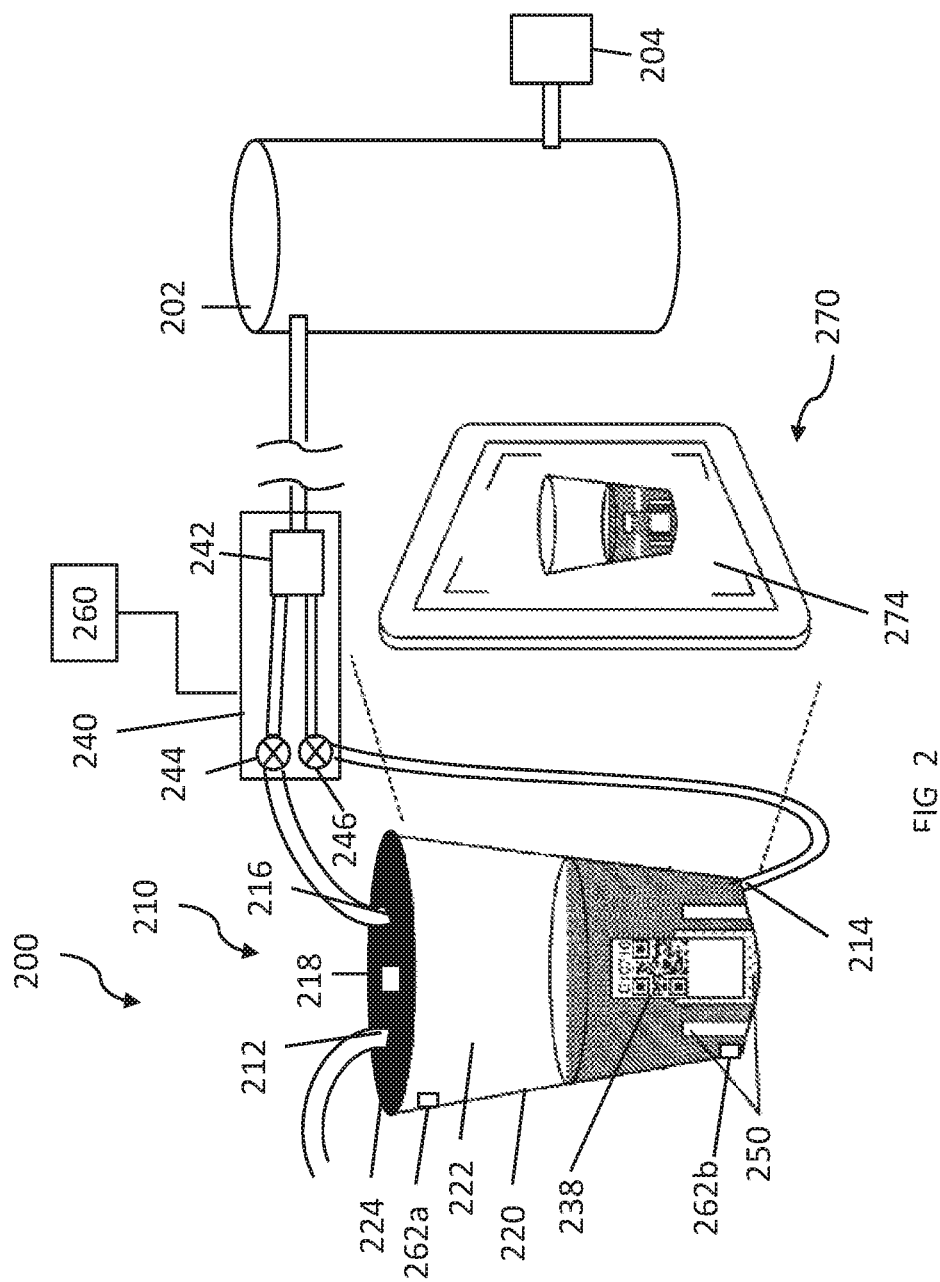
FIG. 2 is a schematic of another variation of the system for assessing fluids from a patient.

The receptacle is configured to receive and accumulate patient fluids (e.g., from a fluid retrieval device, as well as to allow the accumulated patient fluids to drain. Generally, as shown in FIG. 2, the receptacle may include a body 220 defining an internal volume 222 that accumulates fluids, a top 224, and a plurality of ports in fluid communication with the internal volume 222.

Generally, at least the body of the receptacle may be substantially transparent or translucent to white light. For example, the receptacle may be made of blow-molded polyethylene terephthalate (PET) or injection-molded Poly (methyl methacrylate) (PMMA), though other plastics, glass, or other materials permitting visible light transmission may be used. In some variations, the receptacle material may be rigid or semi-rigid so as to withstand suction forces without collapsing. An anti-glare coating, anti-glare finish, or an anti-glare strip (e.g., sticker or decal) may be arranged on a surface of the receptacle.

Figures 4A, 4B:
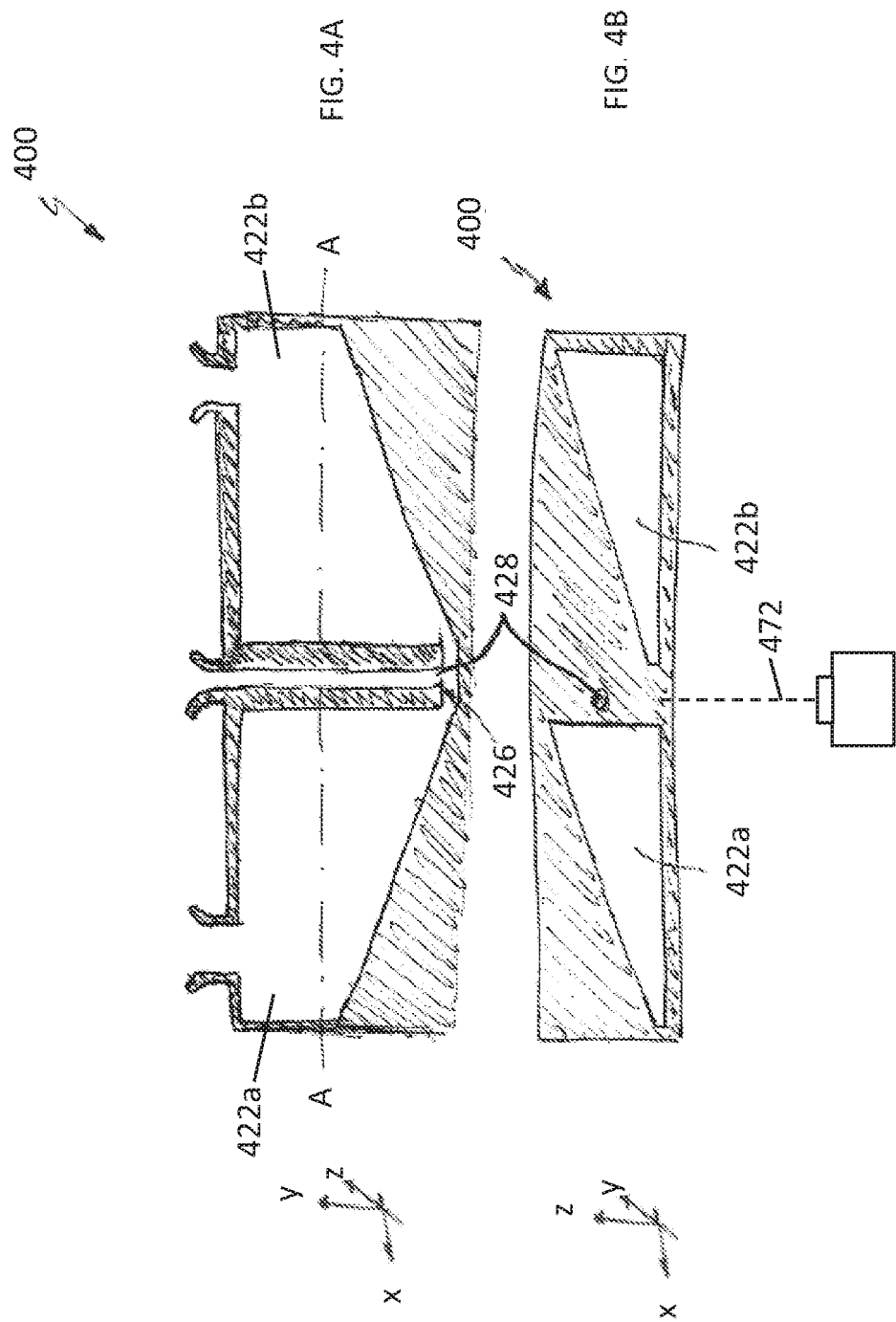
FIGS. 4A and 4B is a side view of one example of a receptacle in a system for assessing fluids from a patient.

The internal volume 222 may be generally frustoconical. Alternatively, the internal volume may be generally prismatic (e.g., generally rectangular prismatic as in FIG. 1, cylindrical, etc.), generally bulbous, or have other suitable general shapes. In some examples, the internal volume 222 may have a capacity of between about 1.0 L and about 3.0 L (e.g., 1.0 mL, 1.5 mL, 3 mL), but it may have any suitable capacity. Furthermore, in some variations the receptacle may include multiple internal volumes or compartments, which may or may not be fluidically coupled. For example, as shown in FIGS. 4A and 4B, the receptacle 400 may include a first internal volume 422*a* and a second internal volume 422*b* that are adjacent to and fluidically coupled to one another.

The receptacle 110 may include one or more slopes that direct fluid volumes to pool in a particular region of the internal volume 122, which may help to more completely drain the receptacle during the flush mode and/or accumulate smaller volumes of fluids together for more accurate analysis of the receptacle contents. The fluids may pool where a lower end of the slope encounters a receptacle wall or where the lower ends of multiple slopes intersect. For instance, a first slope in the receptacle may generally encourage fluid to pool near one side of the bottom of the slope (e.g., toward sump 126 and sump pickup 128, against the receptacle wall as shown in FIG. 1). As another example, a second additional slope in the receptacle may generally encourage fluid to pool where the first and second slopes generally intersect (e.g., at central sump 426 near sump pickup 428, as shown in FIG. 4A). The slope may include a smooth taper as shown in FIG. 4A, or include a series of discrete, stepped sections.

The receptacle may further include one or more internal baffles or other features to help prevent incoming fluids (e.g., entering through inlet port 112) from moving directly into the third port 116 during the fill mode.

The top 224 may provide a substantially fluid-tight seal for the internal volume. The top 224 may be integral with the body 220 of the receptacle, or alternatively may be coupled to the body 220 of the receptacle 210. For instance, the lid may be threaded for mating with the body 220, or include locking tabs or other locking features that allow the lid to be snapped or otherwise sealed onto the body 220. The top 224 may include additional sealing features such as a gasket. Furthermore, the top 224 may include caps or other covers to seal one or more of the ports before and/or after the receptacle is used during the surgical procedure (e.g., during storage or disposal of the receptacle 210).

The system may further include a holder configured to receive the receptacle. In these variations, the receptacle may be a liner that is placed inside the holder, and, in some instances, the receptacle may be designed to be single-use or disposable while the holder may be designed to be reusable. The holder may be substantially rigid or semi rigid, while the receptacle may be more flexible than the holder. In some variations, the holder may include a canister, cup, or other outer container with an internal recess that receives and holds the receptacle. In other variations, the holder may additionally or alternatively include a framework (e.g., lattice, one or more rings, etc.) creating an internal space that receives and holds the receptacle Like the receptacle, the holder may include a material that is substantially transparent or translucent to white light.

Ports

As shown in FIG. 1, the receptacle 110 may include a plurality of ports, including an inlet port 112, outlet port 114, third port 116, and/or fourth port 118 or more. One or more of the ports may include a fitting that is configured to fluidically couple to tubing. For example, the fitting may include a member with a lumen, where tubing may telescopically and frictionally engage with the member such that contents of the tubing pass into the lumen of the fitting and vice versa. Some or all of the ports may be located at or near the top of the receptacle, while additionally or alternatively at least one port may be located elsewhere in the receptacle. For instance, as shown in FIG. 2, the inlet port 112 and third port 116 are located in the top 224 of the receptacle, while the outlet port 114 is located near the bottom of the receptacle body 220.

The inlet port functions to pass fluids into the receptacle. In particular, as shown in FIG. 1, the inlet port 112 may be fluidically coupled via tubing to a fluid retrieval device 108 or other fluid source, and allow transfer of fluids from the fluid retrieval device 108 or other fluid source into the receptacle. The inlet port may include a valve that opens and closes to regulate flow through the inlet port, and/or substantially prevents fluids from traveling in a reverse direction out of the receptacle through the inlet port (e.g., a one-way valve). Furthermore, the receptacle may include multiple inlet ports, which may, for example, enable faster accumulation of fluids in the receptacle, performed in parallel.

The outlet port functions to drain fluids from the receptacle when the system is operating in the flush mode. In particular, the outlet port may be fluidically coupled via tubing to a second receptacle, such as for disposal of the fluids, and allow transfer of fluids from the first receptacle to the second receptacle. In one variation, as shown in FIG. 1, the outlet port 114 may be located at or near the top of the receptacle 110. In this variation, the receptacle may include a sump 126 in a lower region of the internal volume 122 where fluid tends to pool, and a sump pickup 128 that places the sump 126 in fluidic communication with the outlet 114. The sump pickup 128 may be tubing or other member with a lumen, having one end located adjacent to the sump 126 and another end coupled to the outlet port 114. Upon application of suction to the outlet port 114, fluid in the sump 126 may be drawn up the sump pickup 128, and through the outlet port 114 out of the receptacle 110.

In another variation, as shown in FIG. 2, the outlet port 214 may be located at or near the bottom of the receptacle 210. Fluid collected in a lower region of the internal volume 222 may drain directly out the outlet port 214 out of the receptacle as a result of gravity and/or suction during the flush mode.

The outlet port may include a valve that opens and closes to regulate flow through the outlet port, and/or substantially prevent fluids from traveling in a reverse direction back into the receptacle through the outlet port (e.g., a one-way valve). Furthermore, it should be appreciated that the receptacle may include multiple outlet ports. For instance, the outlet port arrangements shown in FIGS. 1 and 2 may be combined, such as with a first outlet port arranged in combination with a sump pickup as shown in FIG. 1 and a second outlet port arranged as shown in FIG. 2. Multiple outlet ports may, for example, facilitate faster draining performed in parallel, provide redundancy in case of a clog, or provide different options that may be better for different kinds of fluids (e.g., fluids with different viscosities).

The third port functions to pass suction from a vacuum source into the receptacle when the system is operating in the fill mode, where suction can thereby be communicated within the receptacle to draw fluids through the inlet port into the receptacle. For instance, as shown in FIG. 1, when the system is operating in the fill mode, suction from vacuum source 106 (which may be communicated through second receptacle 102) is communicated via tubing through the third port 116 and into the receptacle 110. Because the receptacle 110 may be a substantially fluid-tight volume, the suction in receptacle 110 is also communicated through inlet port 112, such that fluid is drawn from fluid retrieval device 108 (or other fluid source) through the inlet port 112 and into the receptacle 110.

The receptacle may further include a fourth port, which functions as a vent to facilitate draining of the fluid through the outlet port when the system is operating in the flush mode. The fourth port may be located on the receptacle such that it is substantially opposite to the accumulated volume of fluid in the receptacle, in order to provide a pressure differential facilitating the draining of the fluid. For instance, as shown in FIG. 1, the fourth port 118 may be located at or near the top of the receptacle, while the fluid accumulates in the sump 126. Similarly, as shown in FIG. 2, the fourth port 218 may be located at or near the top of the receptacle, while the fluid accumulates in the body 220.

Optical Fiducial

As shown in FIG. 2, the receptacle may include one or more optical fiducials 238. The optical fiducial may be coupled to or integral with the receptacle or the packaging of the receptacle, and be associated with receptacle-related information. For example, the optical fiducial may be adhered to a surface of the receptacle or packaging, printed onto a surface of the receptacle or packaging, molded or etched into the receptacle or packaging, or associated with the receptacle or packaging in any suitable manner. The fiducial can, for example, include a quick-response (QR) code, a barcode, alphanumerical code, symbolic marker, or other optical identification marker suitable for identifying or communicating a receptacle type and/or receptacle-related information. Receptacle-related information, which may be accessed by scanning or looking up the fiducial in a database, may include, for instance, a type of the receptacle, geometry and/or dimensions of an internal volume of the receptacle, etc.

The optical fiducial may include a color fiducial. The color fiducial may be coupled to or integral with the receptacle or its packaging, and be associated with color-related information to enable color normalization of the images of the fluid in the receptacle, such as to compensate for variations in lighting conditions. In one variation, the color fiducial may display one or more red hues, each of which has an assigned or known color value. For example, different hues may be displayed and arranged in different boxes or segments in a grid, strip, ring, color wheel, or any suitable shape for displaying color-normalizing information. Furthermore, the color fiducial may be in the form of a decal, sticker, ring or other component configured to couple to the receptacle or receptacle packaging, or any component suitable for associating the color fiducial with the receptacle or its packaging. The images of fluid in the receptacle can be color-adjusted (e.g., adjustment of exposure, contrast, saturation, temperature, tint, etc.) until an imaged color fiducial has a color value matching the assigned or known color value of the color fiducial.

Valve System

The valve system functions to toggle the system between the fill mode and the flush mode. The valve system includes at least one valve that redirects suction from a vacuum source such that the suction may be used to alternately draw fluid into the receptacle during the fill mode, and to draw fluid out of the receptacle during the flush mode.

Fill and Flush Modes

Generally in the fill mode, the valve system directs suction from a vacuum source through the third port of the receptacle into the internal volume of the receptacle, thereby drawing fluid through the inlet port of the receptacle into the internal volume of the receptacle. Furthermore, generally in the flush mode, the valve system directs suction from the vacuum source through the outlet port of the receptacle, thereby drawing fluid through the outlet port out of the internal volume of the receptacle.

For example, as shown in FIG. 1, the valve system 140 may include a valve 142 to direct suction from a vacuum source. Valve 142 may be a three-port valve that has a first valve port 142a coupled to a vacuum source 104 (providing a vacuum communicated through second receptacle 102 and controlled by vacuum regulator 106), a second valve port 142b regulating a fluidic path to port 116 of the receptacle, and a third valve port 142c regulating a fluidic path to the outlet port 114 of the receptacle. The valve 142 selectively fluidically connects the first valve port 142a with either the second valve port 142b or the third valve port 142c (to join with either the fluidic path to port 116 or the fluidic path to outlet port 114), depending on which mode the valve system is operating in. Furthermore, the valve system may include additional valves coupled to inlet 112, outlet 114 and/or fourth port 118, which are either closed or open, depending on which mode the valve system is operating in.

In this example, when the valve system is operating in the fill mode (shown in FIG. 1), the valve 142 fluidically connects the first valve port 142a with the second valve port 142 b, thereby directing suction from the vacuum source 104 through port 116 of the receptacle. The valve coupled to the inlet port 112, if present, is open to enable the fluid retrieval device, while the valve coupled to the outlet port 114, if present, is closed. Additionally, the valve coupled to the fourth port 118 is closed, such that the suction is communicated through the internal volume 122 to inlet port 112, which draws fluid from fluid retrieval device 108 (or other fluid source) into the internal volume 122 of the receptacle. Conversely, when the valve system is operating in the flush mode, the valve 142 is adjusted so as to fluidically connect the first valve port 142a with the third valve port 142c, thereby directing suction from the vacuum source 104 through the outlet port 114 of the receptacle. The valve coupled to the inlet 112, if present, is closed to disable the fluid retrieval device, while the valve coupled to the outlet 114, if present, is open. Additionally, the valve coupled to the fourth port 118 is open, such that the internal volume 122 is vented open to ambient pressure and there is a pressure differential facilitating the draining of the fluid through outlet port 114.

In another example, as shown in FIG. 2, the valve system 240 may include more than one valve to direct suction from a vacuum source. In particular, valve system 240 may include a flow divider 242 that is coupled to a vacuum source 204 (through second receptacle 202). The flow divider 242 divides into one flow branch toward valve 244 regulating a fluidic path to port 216 of the receptacle, and another flow branch toward valve 246 regulating a fluidic path to outlet port 214 of the receptacle. Either one of the valve 244 or valve 246 may be open, depending on which mode the valve system is operating in. Furthermore, the valve system may further include additional valves coupled to inlet port 212, outlet port 214 and/or fourth port 218, which are either closed or open, depending on which mode the valve system is operating in.

In this example, when the valve system is operating in the fill mode, the valve 244 is open and the valve 246 is closed, thereby directing suction from the vacuum source 204 through valve 244 and port 216 of the receptacle. The valve coupled to the inlet port 212, if present, is open to enable the fluid retrieval device, while the valve coupled to the outlet port 214, if present, is closed. Additionally, the valve coupled to the fourth port 218 is closed, such that the suction is communicated through the internal volume 222 to inlet port 212, which draws fluid from fluid retrieval device (or other fluid source) into the internal volume 222 of the receptacle. Conversely, when the valve system is operating in the flush mode, the valve 244 is closed and the valve 246 is open, thereby directing suction from the vacuum source 204 through valve 246 and the outlet port 214 of the receptacle. The valve coupled to the inlet port 212, if present, is closed to disable the fluid retrieval device, while the valve coupled to the outlet port 214, if present, is open. Additionally, the valve coupled to the fourth port 218 is open, such that the internal volume 222 is vented open to ambient pressure and there is a pressure differential facilitating the draining of the fluid through outlet port 214. Furthermore, in some variations, both valves 244 and 246 may be closed to suspend the communication of suction into the receptacle (e.g., during image capture of fluid in the receptacle).

In other variations, the valve system may include other suitable combinations of valves that enable rerouting of suction from the vacuum source to fill and empty the receptacle.

Actuation

In one variation, at least part of the valve system may be automatically controlled (e.g., by a controller as further described below). For example, the valve system may include an electromagnetic actuator (e.g., solenoid) that selectively opens and closes one or more valves between valve configurations for the fill and flush modes. As another example, the valve system may include a passive, automatic mechanical or magnetic actuator. Such automatically controlled valve systems may be based on sensor signals that trigger the fill and/or flush modes, as further described below. However, any suitable actuating device may be used to automatically actuate one or more of the valves in the valve system.

In another variation, at least part of the valve system may additionally or alternatively be manually controlled by a user. For instance, the valve system may include a manual actuator (e.g., lever, handle, wheel, button, plunger, switch, etc.) in order to adjust one or more valves between valve configurations for the fill and flush modes. The particular kind of manual actuation may vary, for example, on the type of valve (e.g., ball valve, butterfly valve, gate valve, diaphragm valve, etc.), though the valve system may include any suitable interface for actuating one or valves in the valve system based on user input. In these variations, the system may provide audible and/or visual instructions or warnings that prompt a user to actuate the valve system between the fill and flush modes.

Camera

As shown in FIG. 1, the system may include a camera 172 that generates images of the fluid in the receptacle. The camera may be configured to automatically generate images on a predetermined schedule (e.g., periodically or every time a predetermined volume of fluid has been added or accumulated in the receptacle), and/or generate images based on user input (e.g., whenever a user provides manual instructions for an image to be generated of the fluid, such by input on a user interface display).

The camera may include at least one optical image sensor (e.g., CCD, CMOS, etc.) that captures a color optical digital image with red, green, and blue (RGB) color components for the pixels, and/or other suitable optical components. For example, the camera may include a single image sensor paired with suitable corresponding optics and/or filters (e.g., color filter arrays such as a Bayer pattern filter). As another example, the camera may include multiple image sensors paired with suitable corresponding optics, such as at least one prism or diffractive surface to divide white light into separate color channels (e.g., RGB), each of which is detected by a respective image sensor. However, the camera 172 may include any suitable image sensors and other optics components to enable the camera to generate images of the fluid in the receptacle.

The camera may be configured to transmit the images to a processor for analysis, and/or to a database that stores the images, through a wired or wireless connection. As shown in FIG. 1, the camera 172 may be part of a handheld or mobile device (e.g., tablet, mobile smartphone, etc.), though in other variations the camera may a standalone device that communicates images to other separate computing devices or database using a wired or wireless connection.

Sensors

The system may further include one or more sensors configured to detect the volume of fluids in the receptacle and to generate a fluid level signal based on the detection of fluid volume or fluid level in the receptacle. The fluid level signal may be used to trigger the actuation or toggling between the fill and flush modes of the valve system, and/or to estimate fluid volume in the receptacle (e.g., for estimation of current or cumulative quantity of blood volume and/or quantity of blood component lost by the patient). The sensors may include fluid level sensors coupled to the receptacle or near the receptacle. Additionally or alternatively, the camera generating images of the fluids in the receptacle may be treated as a sensor, in that the images may be analyzed to detect fluid level.

Fluid Level Sensors

The system may include one or more point-level sensors that indicate whether the fluid level in the receptacle is above or below a particular threshold sensing point. For example, one or more fluid level sensors may include a binary fluid level sensor that outputs a fluid level signal (e.g., voltage) of one value when the sensor detects a fluid volume not satisfying a threshold, and outputs a fluid level signal of another value when the sensor detects a fluid volume satisfying the threshold.

In one variation with point-level sensors, the system may include one or more sensors configured to detect at a high threshold volume of fluids in the receptacle and generate a fluid level signal indicating the high threshold fluid volume. For instance, as shown in FIG. 2, the system may include a fluid level sensor 262 a coupled to the receptacle 210 near or at the top of internal volume 222, and configured to detect a fluid volume above the high threshold fluid volume (e.g., a fluid level above the location of the sensor 262 a). A fluid level signal indicating the high threshold fluid volume may be used to trigger the flush mode of the valve system and/or trigger the camera to generate an image of the fluid in the receptacle. The high threshold fluid volume can be about full capacity of the receptacle or near full capacity, such as about 3 L, or any suitable value.

In another variation with point-level sensors, the system may additionally or alternatively include one or more sensors configured to detect a low threshold volume of fluids in the receptacle and generate a fluid level signal indicating the low threshold fluid volume. For instance, as shown in FIG. 2, the system may include a second fluid level sensor 262 b coupled to the receptacle 210 near or at the bottom of internal volume 222, and configured to detect a low threshold volume of fluids in the receptacle below a low threshold volume of fluids in the receptacle (e.g., a fluid level below the location of the sensor 262 b). A fluid level signal indicating the low threshold fluid volume may be used to trigger the fill mode of the valve system. The low threshold fluid volume can be about zero or near zero, or any suitable value.

Similarly, the system may include additional point-level sensors at discrete fluid level locations to provide additional information, such as regarding one or more intermediate fluid levels between a low threshold and a high threshold. Fluid level signals indicating intermediate fluid volumes may be used to trigger the camera to generate an image of the fluid in the receptacle as the receptacle fills with fluid. Additionally or alternatively, fluid level signals indicating intermediate fluid volumes may provide more frequent updates for estimates of the volume of fluid in the receptacle.

The system may include one or more continuous-level sensors that measure the fluid level in the receptacle and indicate a numerical value corresponding to fluid volume. For instance, a continuous-level sensor may output a fluid level signal (e.g., voltage) within a range corresponding to a measurable range of fluid volumes. As the receptacle is filled or drained, the particular value for the fluid level signal may be continually compared to a high threshold fluid volume and/or a low threshold fluid volume to determine whether the fluid volume in the receptacle satisfies either threshold. Furthermore, the particular value for the fluid level signal may be compared to other thresholds to trigger the camera to generate an image of the fluid in the receptacle, as the receptacle fills with fluid (e.g., every 5 mL added to the receptacle may trigger the camera).

Any suitable fluid level sensor may be used to detect fluid volume in the receptacle and generate a fluid level signal that indicates the detected fluid volume. For example, capacitance level sensors, conductive level sensors, ultrasonic level sensors, and/or optical sensors, etc. may be appropriate as point-level and/or continuous-level sensors. Furthermore, the system may additionally or alternatively include a magnetic float having a magnet sealed within. As fluid accumulates in the receptacle, the float may rise relative to one or more magnetic sensing points corresponding to threshold fluid volumes, which may, for example automatically trigger via a magnetic "signal" that automatically (e.g., mechanically) triggers toggling of fill and flush modes. Similarly, the system may additionally or alternatively include a mechanical sensor, such as a float mechanically coupled (e.g., with a lever) to the valve system such that as the float rises relative to one or more predetermined points corresponding to threshold fluid volumes, the float may automatically trigger via a mechanical "signal" that automatically triggers toggling of fill and flush modes.

Image Analysis for Fluid Level Detection

In another variation, fluid level may be detected by analyzing images of the fluid in the receptacle. For example, the camera can repeatedly capture images of the receptacle (e.g., every two seconds) and a processor may employ machine vision techniques, such as edge detection, to estimate fluid volume (e.g., determine whether the fluid volume depicted in each image satisfies a particular high or low threshold volume of fluids, and/or absolute quantity of fluid). In this variation, the fluid level signal may be generated by a processor embodied in, for example, a handheld or mobile device 170 that is separate from the receptacle.

Furthermore, the system may detect the volume of fluids in the receptacle based on any suitable combination of the above-described techniques. For example, the system can include a float having a color (e.g., green) generally contrasting to the color of patient fluids, which may enable identification of the float in an image using machine vision techniques. The identified position of the float in the images can be used, such as by comparing the float to optical fiducials, to estimate fluid volume and determine whether there is a high threshold fluid volume or low threshold volume fluid volume in the receptacle.

Controller

Particularly in variations in which the valve system is automatically actuated, the system may further include a controller configured to actuate the valve system to toggle between the fill mode and the flush mode. More specifically, the controller may be configured to actuate the valve system based on the fluid level signal generated by the one or more sensors in the sensor system.

For example, as shown in FIG. 2, the system may include a controller 260 coupled to the valve system 240, such that the controller 260 may receive fluid level signals wirelessly and/or through a wired connection. Controller 260 may be configured to receive at least one fluid level signal from sensor 262 *a*, sensor 262 *b*, and/or from mobile device 270, and actuate the valve system as described above based on a fluid level signal indicating a volume of fluids detected in the receptacle. In particular, upon receiving a fluid level signal indicating a high threshold fluid volume in the receptacle, the controller 260 may actuate the valve system 240 such that the system is operating in the flush mode. In one variation, the controller 260 may maintain the system in the flush mode for a predetermined period of time (e.g., 30 seconds). In another variation, the controller 260 may maintain the system in the flush mode until the controller 260 receives at least one fluid level signal indicating a low threshold volume of fluids in the receptacle (e.g., zero or close to zero). Upon receiving a fluid level signal indicating a low threshold fluid volume in the receptacle, the controller 260 may actuate the valve system 240 such that the system is again operating in the fill mode. The controller 260 may similarly continue to toggle between the fill and flush modes based on the fluid level signals it receives.

The controller may additionally or alternatively be configured to control when the camera generates images of the fluid in the receptacle. In one variation, the controller 260 may trigger the camera to generate images whenever the receptacle is sufficiently full of fluid. For example, upon receiving a fluid level signal indicating a high threshold volume of fluid, the controller 260 may trigger the camera to generate images of the fluids in the receptacle. In another variation, the controller 260 may trigger the camera to periodically or intermittently generate images (e.g., every two seconds, every 5 mL of fluid added to the receptacle). In one or both of these variations, prior to triggering the camera, the controller 260 may additionally actuate part of the valve system 240 (e.g., close a valve coupled to inlet port 212 to disable the fluid retrieval device, open a valve coupled to the port 218 to open the internal volume 222 to ambient pressure, etc.) and/or wait a predetermined period of time (e.g., five seconds) to allow fluids in the receptacle to settle before generating the image of the fluids.

Imaging Aid

The system may include one or more features in or around the receptacle to aid in optical imaging of fluids. For example, one feature to aid in optical imaging may include an insert or light source arranged within the internal volume of the receptacle. As another example, the receptacle may define one or more slopes that further define the internal volume.

Insert

The system may include an insert arranged within the internal volume of receptacle, such as at or near a bottom of the internal volume. The insert may, for example, backscatter light through the fluid and improve the quality of images from which fluid-related information may be derived. In some variations, the insert and a surface of the receptacle may cooperate to define a first region with substantially uniform thickness such that fluid in the first region exhibits substantially uniform color. Pixel color values in image portions depicting the first region may, for example, be correlated to a blood component concentration (e.g., with template matching techniques, parametric modeling techniques described in further detail below). In particular, the insert may include a first feature that is substantially parallel to and offset from a surface of the receptacle, such that the first feature cooperates with the surface of the receptacle to form the first region of substantially uniform thickness. For example, the first feature may include an arcuate surface (e.g., the insert may be circular, semi-circular, or otherwise curved) in instances in which the receptacle surface is similarly arcuate (e.g., generally cylindrical). As another example, the first feature may include a generally planar wall (e.g., the insert may be at least a segment of a polygonal prism) in instances in which the receptacle surface is planar (e.g., rectangular tank). However, the insert may include any suitable features that generally track a surface of the receptacle so as to define a region of substantially uniform thickness between the insert and the surface of the receptacle.

The insert and a surface of the receptacle may additionally or alternatively cooperate to define a second region in which fluid exhibits a color gradient. Pixel color values in image portions depicting the second region may, for example, be correlated to a hemolysis level in the blood (e.g., with template matching techniques, parametric modeling techniques). To compensate for the effect of hemolysis on perceived pixel color value in images (e.g., due to different light scattering characteristics of whole red blood cells and free hemoglobin), algorithms and processes for evaluating images may be adjusted based on the known hemolysis concentration. In particular, the insert may include a second feature that generally tapers away from a surface of the receptacle, such that the second feature cooperates with the surface of the receptacle to form the second region in which fluid has a color gradient. For example, the second feature may have a surface with a linear profile, a non-linear profile, a stepwise function profile, etc. that generally angles away from the surface of the receptacle. However, the insert may include any suitable features that generally taper or angle away from a surface of the receptacle so as to define a region in which fluid has a color gradient between the insert and the surface of the receptacle.

Figure 3A:
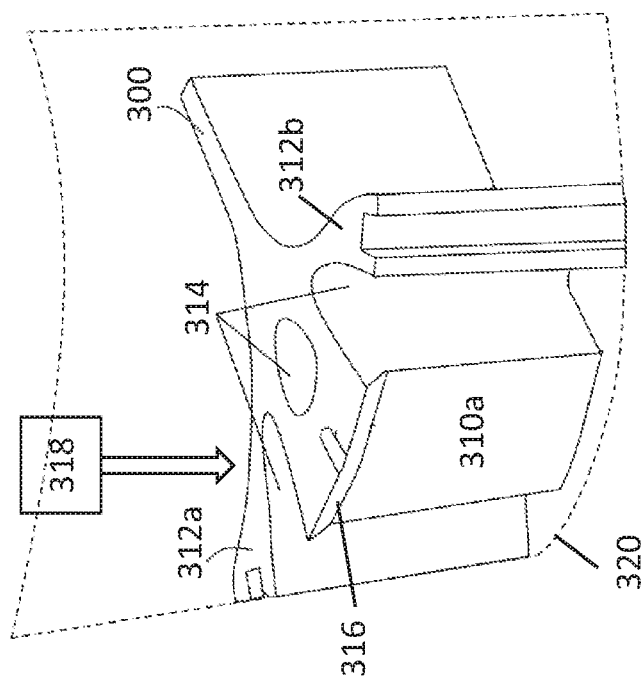
FIGS. 3A-3C are schematics of variations of an insert used to aid optical imaging.

For instance, as shown in FIG. 2, the system may include an insert 250 that is proximate to a wall of the receptacle 210. As shown in FIG. 3A, one variation of the insert 300 *a*

(similar to insert 250) may cooperate with a wall of the receptacle to define a region of substantially uniform thickness. In particular, the insert 300 a may include an insert surface 310 offset from a receptacle surface 320, such that a region of substantially uniform thickness is formed between the insert surface 310 a and the receptacle surface 320. Fluids accumulated in the receptacle may generally surround the insert 300 a (e.g., through gaps 314), including in the region of substantially uniform thickness, where fluids exhibit a substantially uniform color. Images of the fluid in the receptacle include an image region corresponding to the region of substantially uniform thickness, and the pixel color values in the image region may then be correlated to a blood component concentration estimate (e.g., using template techniques, parametric modeling techniques, etc. as further described below).

The insert 300 a may be coupled to the receptacle. For example, the members 312 a and 312 b (and/or other portions of the insert) may be coupled to the receptacle wall 320 with fasteners (e.g., epoxy, magnets, etc.). As another example, the members 312 a and 312 b (and/or other portions of the insert) may be coupled to the receptacle wall 320 without fasteners, such as by press-fit or snap-fit. Additionally or alternatively, the members 312 a and 312 b (and/or other portions of the insert) may include features that interlock with complementary features on the receptacle surface 320 (e.g., splines and notches, dovetails, etc.). Such coupling may be substantially permanent or removable. For instance, in some variations, the insert may be removable from the receptacle for reuse. Alternatively, the insert 300 a may be integrally formed with the receptacle (e.g., by injection molding or blow molding techniques).

Figure 3C:
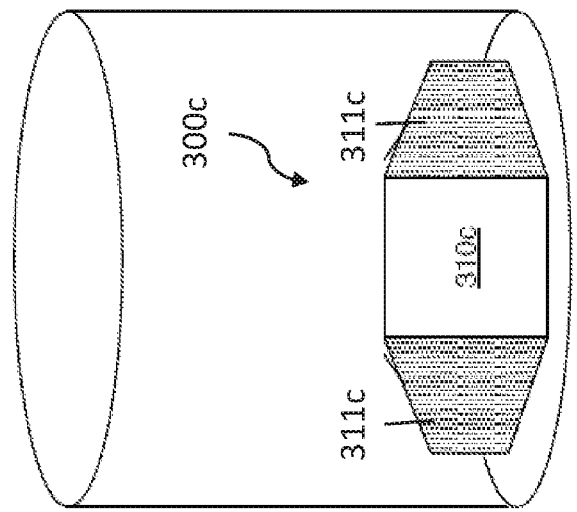
Figure 3B:
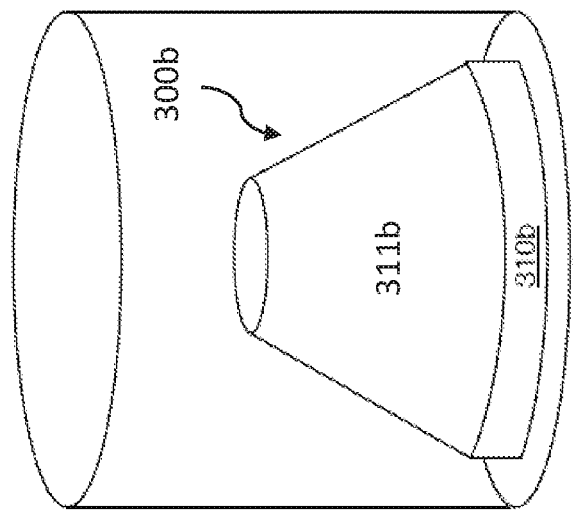

In another variation as shown in FIG. 3B, the insert 300 b includes a first insert surface 310 b and second insert surface 311 b (on frustoconical portion of 300 b). The first insert surface 310 b is offset from a receptacle wall such that a first ring-shaped region of substantially uniform thickness is formed between the first insert surface 310 b and the receptacle wall. In this first region, the fluid may have a substantially uniform color. The second insert surface 311 b is tapered (e.g., with a linear or non-linear profile) toward a central axis of the receptacle, such that the second insert surface 311 b cooperates with the receptacle wall to provide a second region in which fluid exhibits a visual color gradient. In the second region, fluid appears progressively darker in a color gradient pattern as the thickness in the second region increases.

In another variation as shown in FIG. 3C, the insert 300 c includes a first insert surface 310 c offset from a receptacle surface, such that a first region of substantially uniform thickness is formed between the insert surface 310 c and the receptacle wall. In this first region, fluid may have a substantially uniform color. The insert 300 c also includes one or more second surfaces 311 c that cooperate with the receptacle wall to provide a second region in which fluid exhibits a visual color gradient. As with insert 300 b, in the second region, fluid appears progressively darker in a color gradient pattern as the thickness in the second region increases.

The insert (or at least the surfaces 310) may include a material or coating that is white, substantially opaque, and generally impermeable to fluid. For instance, the insert may be made of injection-molded white plastic. The insert may alternatively include a color or pattern (e.g., grid, matrix barcode, QR code) that is observable (e.g., on surfaces 310) through the fluid. For instance, a color grid or matrix bar code coupled to the insert and observable through the receptacle surface 320 and fluid can be used to determine fluid parameters (e.g., fluid component concentrations) associated with fluid within the receptacle. For example, in one application, a color grid including a set of regions of color, each region associated with a blood component concentration value, can be applied to the insert. In this application, when a particular region of the color grid from the fluid is substantially visually indistinguishable from the fluid within the canister, the blood component concentration value associated with that region of the color grid can be taken as an estimated blood component concentration of the fluid. Similarly, a color pattern exhibiting a gradient in color (e.g., by including a pattern having successively blurrier edges between regions of the pattern) can be used to assess a level of hemolysis, in relation to a color gradient within fluid in the receptacle.

Light Source

The system may include a light source 318 configured to transmit light through a portion of fluid within the canister, which may, for example, help generate an optical image with a color gradient from which a hemolysis level of the fluid can be estimated. In the variation shown in FIG. 3, the light source 318 may be coupled to the receptacle so as to direct light downward toward the bottom of the receptacle. Light incident on the surface of the fluid penetrates the surface of the fluid and is absorbed by the fluid as a function of both depth and an absorption coefficient of the fluid, wherein the absorption coefficient of the fluid is affected by both a concentration of a substance in the fluid and a type or size of the substance (e.g., either a whole red blood cell or free hemoglobin and ruptured cell matter). Thus, though generally fluid in the receptacle may be substantially uniform in particulate concentration and distribution, the illuminated fluid may appear visually lighter at the surface of the fluid and progressively darker at deeper portions of the fluid in a vertical color gradient pattern. The particular characteristics of the vertical color gradient pattern may be used to generate a metric of the absorption of light by the fluid, which can in turn be used to assess a level of hemolysis in the fluid. Similar color gradient patterns may be generated elsewhere in the fluid volume, such as a horizontal color gradient pattern. For instance, the light source 318 may be coupled to the insert described above, to generate a color gradient pattern along any suitable direction in the fluid. Generally, the color gradient pattern may be correlated to a level of hemolysis (e.g., percentage) in the fluid using template matching techniques, parametric modeling techniques, etc.

The light source (e.g., LED or laser) may emit wavelengths of light spanning or otherwise associated with one or more absorbance peaks in an absorbance spectrum for one or more target components of fluid in the receptacle. For instance, the light source 318 may be configured to provide a broad range, narrower range, or discrete waveband of light corresponding to absorbance peaks of one or more blood components. For example, in relation to hemoglobin, the light source 318 may be configured to provide wavelengths of light from about 400 nm to about 700 nm and between about 800 nm to about 950 nm. Additionally or alternatively, in relation to hemoglobin, the light source 318 can be configured to provide wavelengths of light associated with absorbance peaks/spectra of one or more forms of hemoglobin (e.g., oxygenated hemoglobin, sulfhemoglobin, methemoglobin, etc.) in order to enable differentiation in colors of fluid and/or color gradients of fluid associated with different forms of hemoglobin. However, the light source 318 may additionally or alternatively emit light of any suitable wavelengths corresponding to other types of blood component absorbance spectra.

In other variations, the insert 300 and/or light source 318 may be similar to any of the variations described in U.S. Patent Pub. 2015/0294461, entitled "METHOD FOR ESTIMATING A QUANTITY OF A BLOOD COMPONENT IN A FLUID CANISTER," which is hereby incorporated in its entirety by this reference.

Internal Volume with Varying Dimensions

The internal volume of the receptacle may have varying dimensions along one or more axes, to help improve the analysis of fluids of having high or low concentrations of red blood cells (RBC) or hemoglobin (or other blood component).

As shown in FIG. 4B, at least a portion of an internal volume 422 a and/or 422 b of the receptacle may include a shallow section (as measured along the camera optical axis 472) so as to improve the analysis of fluids having a high concentration of RBCs or hemoglobin. This feature may be helpful because in instances in which blood has a high RBC concentration, a deep or thick volume of the blood may be too opaque or optically "dark" for useful pixel color visualization in an image of the blood. This is because a deep or thick volume of blood having a high RBC concentration may scatter and/or absorb nearly all incident light, leading to insufficient light transmission through the blood. Consequently, such opacity may limit the amount of blood component concentration information that may be derived from an image of the blood. Furthermore, blood with higher RBC concentrations must be imaged in shallower or thinner volumes in order to decrease opacity (i.e., the volume depth or thickness at which opacity is avoided is generally inversely proportional to the RBC concentration). For example, when each of two fluids of different high RBC concentrations (e.g., 42% RBC by volume and 31% RBC by volume) fills a 1.0 inch deep container, both fluids may be opaque and substantially optically indistinguishable. However, when the same two fluids fill shallower 0.1 inch-deep containers, the two fluids are visually distinct, as the fluid with higher RBC concentration is visually darker than the fluid with lower RBC concentration. Therefore, considering the receptacle 400, to increase the range of high fluid RBC concentrations at which optical images of the fluid in the receptacle can provide useful blood component concentration information, at least a portion of an internal volume (e.g., 422 a and/or 422 b) of the receptacle 400 may include a shallow section, as measured along the camera optical axis 472 (Z-axis as labeled in FIG. 4B).

As shown in FIG. 4B, at least a portion of the internal volume 422 a and/or 422 b of the receptacle may include a deep section (as measured along the camera optical axis 472) so as to improve the analysis of fluids having a low concentration of RBCs or hemoglobin. This feature may be helpful because in instances in which blood has a low RBC concentration, a shallower or thinner volume may be too optically clear, akin to water or saline, for useful pixel color visualization in an image of the blood. This is because a shallow or thin volume of blood having a low RBC concentration may not scatter and/or absorb enough incident light in order for the blood to be optically distinguishable from water, saline, or other low RBC concentration fluids. Consequently, such optical clarity may limit the amount of blood component concentration information that may be derived from an image of the blood. For example, in some instances a fluid with low RBC concentration may not have optically detectable blood components. Furthermore, blood with lower RBC concentrations may have to be imaged in deeper or thicker volumes in order to decrease optical clarity (i.e., the volume depth or thickness at which optical clarity is avoided is generally inversely proportional to the RBC concentration). For example, when each of two fluids of different low RBC concentrations (e.g., 0.1% RBC by volume and 0% RBC by volume) fills a 0.1 inch deep container, both fluids may be substantially clear and optically indistinguishable. However, when the same two fluids fill deeper 1.0 inch-deep containers, the two fluids may be visually distinct, as the first fluid with higher RBC concentration (which requires a deeper depth to appear colored or tinted red) is visually redder than the second fluid with lower RBC concentration, due to having greater aggregate light scattering and/or absorption in the deeper container. Therefore, considering the receptacle 400, to increase the range of low fluid RBC concentrations at which images of the fluid in the receptacle can provide useful blood component concentration information, at least a portion of the internal volume of the receptacle 400 may include a deeper section, as measured along the camera optical axis 472 (Z-axis as labeled in FIG. 4B).

The transition between the shallower and deeper sections of an internal volume 422 a and/or 422 b may be a smooth taper, as shown in FIG. 4B. Additionally or alternatively, at least part of the transition between the shallower and deeper sections may include discrete, stepped sections (along the X-axis as labeled in FIG. 4B).

Processor

The system 100 may include or more processors 176 configured to evaluate images of fluid in the receptacle and estimate fluid-related information. The one or more processors 176 may be configured to execute instructions that are stored in memory such that, when it executes the instructions, the processor 176 performs aspects of the methods described herein. The instructions may be executed by computer-executable components integrated with the application, applet, host, server, network, website, communication service, communication interface, hardware/firmware/software elements of a user computer or mobile device, wristband, smartphone, or any suitable combination thereof. The instructions may be stored on memory or other computer-readable medium such as RAMs, ROMs, flash memory, EEPROMs, optical devices (e.g., CD or DVD), hard drives, floppy drives, or any suitable device.

Generally, as further described below, the processor may transform the image of the fluid to a blood component concentration value by correlating the pixel color values of the fluid in the region to a blood component concentration (e.g., with template matching and/or parametric modeling techniques).

As shown in FIG. 1, the one or more processors may be integrated into a handheld or mobile device 170. In other variations, the one or more processors 176 can be incorporated into a computing device or system, such as a cloud-based computer system, a mainframe computer system, a grid-computer system, or other suitable computer system. Additionally or alternatively, the one or more processors may be incorporated into a remote server that receives the images, analyzes the images to characterize fluids in the receptacle and provide fluid-related information, and/or transmit the fluid-related information to another computing device having a display for displaying the fluid-related information to a user.

Display

The display functions to display or otherwise communicate to a user (e.g., doctor, nurse) information that is generated by the system, including but not limited to patient information, images of the receptacle/fluid, and/or fluid-related information estimated as described herein. As shown in FIG. 1, the display 174 may include a screen on a handle or mobile device, a computer monitor, a television screen, a projector screen, or other suitable display.

The display 174 may be configured to display a user interface that enables the user to interact with displayed information. For example, the user interface may enable the user to select display options (e.g., font, color, language) and/or content (e.g., patient information, fluid-related information, alerts). The display may be user-interactive and include a resistive or capacitive touch screen that is responsive to skin, a stylet, or other user contact. In other examples, the display may be user-interactive via a cursor controlled by a mouse, keyboard, or other suitable user input device for receiving user commands.

The system may additionally or alternatively include an audio system that communicates fluid-related information to the user. The display and/or the audio system may provide alerts upon one or more estimations meeting a threshold (e.g., estimated quantity of fluids or blood component exceeds a threshold), which may be useful to prompt certain actions in response, such as providing a blood transfusion.

Other Variations

Other variations of systems for assessing fluids from a patient may be used in arrangements similar to those depicted in FIG. 1 and FIG. 2 (e.g., in series and in fluidic communication between a fluid retrieval device or other fluid source, and a waste management system or other receptacle).

Manifold Receptacle

In one variation, a system for assessing fluids from a patient may include a manifold receptacle. The manifold receptacle may be generally similar to the receptacle variations described above, except that the manifold receptacle is configured to be inserted into an inlet port of a sealed receptacle such as a waste management system. The manifold receptacle may be configured to be single-use and disposable after use during a surgical procedure.

Flow Divider

Figure 5:
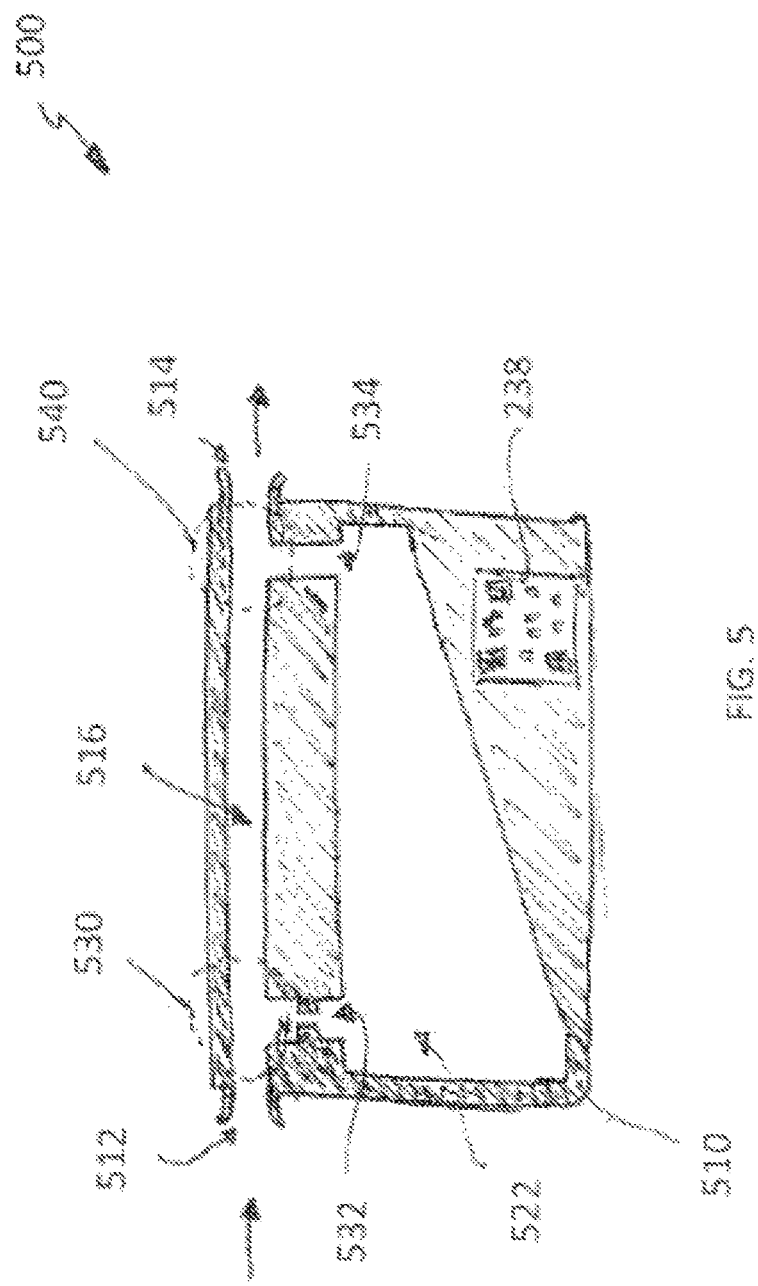
FIG. 5 is a schematic of a variation of a system with a flow divider for assessing fluids from a patient.

As shown in FIG. 5, a system 500 for assessing fluids from a patient may include a flow divider. The flow divider system 500 receives fluid collected by the fluid retrieval device (or from another fluid source), and consistently accumulates in a first receptacle a representative fraction of this fluid for analysis while the rest of the fluid is discarded or otherwise passed to a second receptacle (e.g., waste management system). In other words, as the second receptacle receives fluid of a particular composition (e.g., extracorporeal blood, saline, ascites, bile, irrigant, saliva, gastric fluid, mucus, pleural fluid, urine, etc.), the first receptacle receives a fluid sample having a substantially similar composition of fluids. Assessments of the representative fraction of fluid in the first receptacle may be projected or extended to provide assessments of the total fluid collected by the fluid retrieval device (or from another fluid source).

Generally, a flow divider system 500 for assessing fluids from a patient may include: a receptacle 510 having an internal volume 522 for collecting fluids, and a bypass channel 516 extending between an inlet port 512 and an outlet port 514; and a flow divider 530 that diverts a first predetermined proportion of flow from the inlet port 512 into the internal volume 522 and a second predetermined portion of flow from the inlet port 512 into the bypass channel 516. Generally, the first predetermined proportion of flow into the internal volume 522 is smaller than the second predetermined portion of flow through the bypass channel 516, but in some variations the first and second predetermined proportions may be substantially equal or the first predetermined proportion of flow may be larger than the second predetermined portion of flow. Furthermore, the flow divider system 500 may include a camera and processor similar to those described above.

The internal volume 522 of the receptacle 510 in the system may generally be similar to any of the variations of internal volumes of receptacles described above (e.g., with reference to FIGS. 1-4). For example, as shown in FIG. 5, the receptacle 510 may include one or more slopes to pool fluids toward a particular region of the internal volume 522. Furthermore, like the receptacles described above, the receptacle 510 may include one or more features to aid in optical imaging, such as a fluid insert.

The bypass channel 516 extends between an inlet port 512 configured to be in fluidic communication with a fluid retrieval device or other fluid source, and an outlet port 514 configured to be in fluidic communication with a second receptacle (e.g., waste management system). Additionally, the outlet port 514 may be coupled with a vacuum source, such as a vacuum source associated with a waste management system. Furthermore, in some variations, the inlet port 512 and/or outlet port 514 may include a valve that can be automatically and/or manually controlled to regulate flow in and out of the receptacle 510. For instance, the valves in inlet port 512 and outlet port 514 may be open such that fluid may flow into the internal volume 522 and bypass channel 516. In contrast, the valves may be closed to seal the contents of the receptacle 510. Such sealing may be useful, for example, before or after the surgical procedure for connection/disconnection from a fluid retrieval device and second receptacle, or during transport. As another example, the valves may be closed to allow a user (e.g., a nurse) to safely shake or agitate the receptacle 510 with lowered contamination risk, in order to achieve a more uniform mixing of contents of the receptacle prior to imaging the receptacle. Similarly, caps or other covers may be placed over the inlet port 512 and/or the outlet port 514 to seal the contents of the receptacle 510.

The receptacle 520 may further define a first inner port 532 and a second inner port 534. The first inner port 532 is in fluidic communication with inlet port 512 and the internal volume 522, and functions to pass the first predetermined portion of flow from the inlet port 512 into the internal volume 522. The second inner port 534 is in fluidic communication with the outlet port 514 and the internal volume 522, and functions to pass suction from a vacuum source (coupled to the outlet port 514) into internal volume 522, thereby drawing fluids into the receptacle 510 though the inlet port 512.

The flow divider 530 may be located in the fluid path between (i) the inlet port 512 and (ii) the internal volume 522 and the bypass channel 516. The flow divider functions to consistently divide fluid flowing from inlet port 512 between the internal volume 522 and the bypass channel 516 according to a predetermined flow division ratio (e.g., about 1:20). In particular, the flow divider 530 diverts a first predetermined proportion of flow through first inner port 532 into the internal volume and a second predetermined proportion of flow into the bypass channel 516. For example, for a division ratio of about 1:20, for every one part of incoming fluid that the flow divider 530 diverts into the internal volume, the flow divider 530 may divert about twenty parts of incoming fluid into the bypass channel. However, the flow divider 530 may generally divide flow between the internal volume and the bypass channel according to any suitable flow division ratio.

In one variation, the flow divider 530 may accomplish consistently dividing fluids as a result of the ratio of an effective cross-sectional area of the first inner port 532 relative to the cross-sectional area of the bypass channel 516 (e.g., dimensionally and/or with use of a flow resistor). For example, the cross-sectional area of the first inner port 532 may be smaller than the cross-sectional area of the bypass channel 516, resulting in proportionately less flow diverted through the first inner port 532. As another example, the cross-sectional areas of the first inner port 532 and bypass channel 516 may be substantially similar, but the effective cross-sectional area of the first inner port 532 may be reduced further by a flow resistor (e.g., defining a narrow neck) placed in the first inner port 532.

The receptacle may include an anti-clotting agent, such as heparin. Clotted blood and hemolyzed red blood cells may exhibit different optical characteristics than unclotted blood and whole red blood cells. In view of this difference, an anti-clotting agent, which preserves the integrity of red blood cells collected in the receptacle over time, may help to obtain better quality images from which fluid-related information may be more accurately derived. For example, the internal walls of the internal volume may be coated with an anti-clotting agent, such that as fluid collects in the receptacle and rises up the walls of the internal volume, the fluid is exposed to additional amounts of anti-clotting agents to reduce hemolysis (and extracorporeal clotting) of red blood cells collected in the internal volume. As another example, the receptacle may include a reservoir of anti-clotting agent that can passively drip into the internal volume of the receptacle, and/or be selectively dispensed based on parameters such as volume or "redness" of accumulated fluid in the internal volume, volumetric flow rate of fluid accumulation in the internal volume, etc. Alternatively, the receptacle may include a hemolyzing agent instead of an anti-clotting agent in these arrangements, so as to fully hemolyze fluid in the internal volume, and image analysis (e.g., templates) may be adjusted for hemolyzed blood instead of non-hemolyzed blood.

Furthermore, the fluid divider system may include one or more components enabling fill and flush modes as described in detail above, but may alternatively omit any components operable in such distinct fill and flush modes.

III. Methods for Assessing Fluids from a Patient

Figure 6:
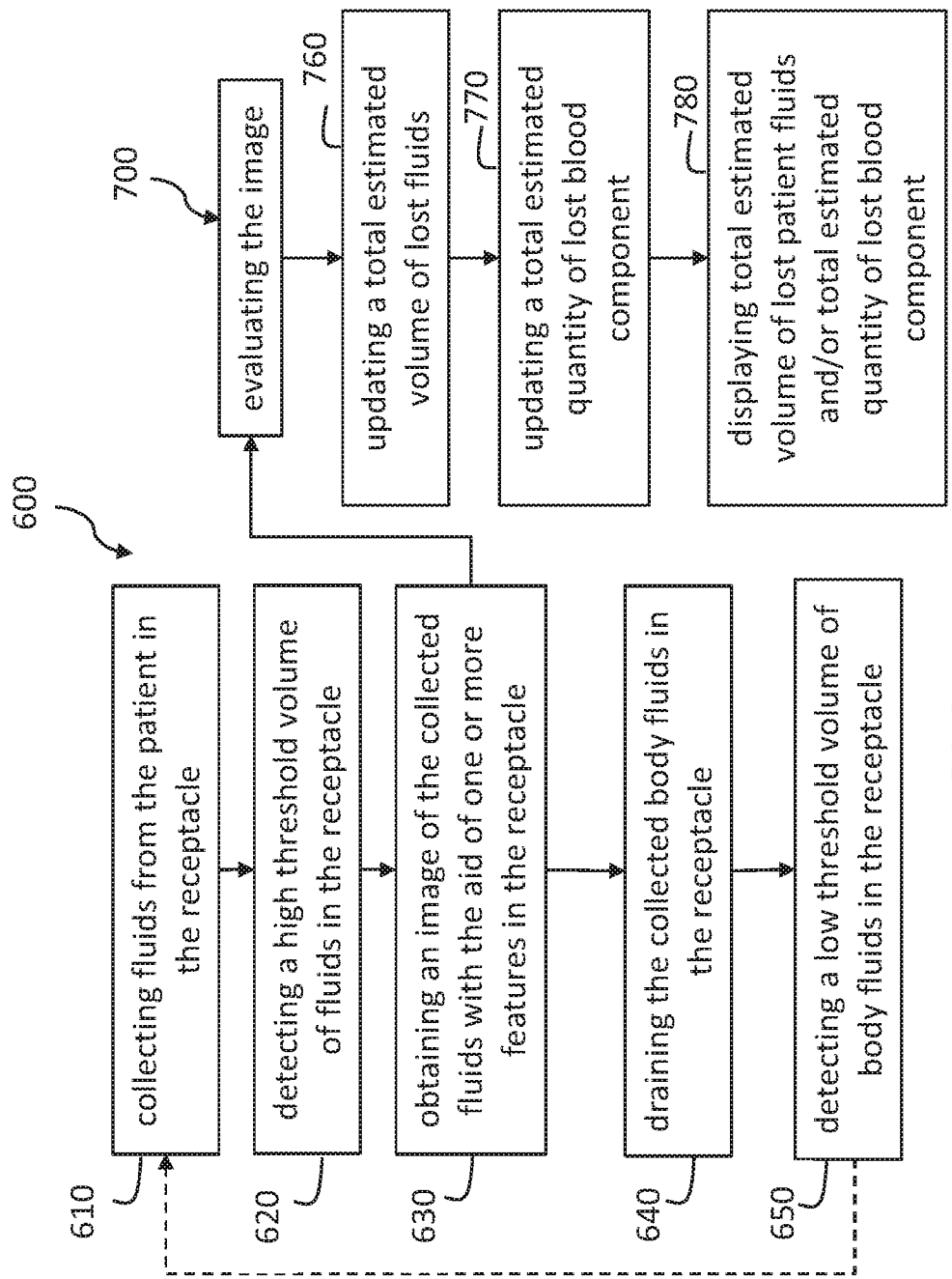
FIG. 6 is a schematic of one variation of a method for assessing fluids from a patient.

Generally, a method for assessing fluids from a patient may be performed with use of a receptacle including an inlet port, an outlet port, and a third port. In some variations, as shown in FIG. 6, a method 600 for assessing fluids from a patient includes: collecting fluids from the patient in the receptacle 610; obtaining an image of the collected fluids 630 with the aid of one or more features in the receptacle; and draining the collected fluids 640 upon reaching a high threshold volume of fluids in the receptacle. The method may further include, upon reaching a low threshold volume of fluids in the receptacle, collecting fluids from the patient in the receptacle. The method may involve actuating a valve system to toggle between collecting fluids and draining fluids which cyclically fills and empties the reservoir, while intermittently obtaining images of the collected fluids.

Additionally, for each image obtained, the method 600 may include evaluating the image 700 to estimate fluid volume and a blood component quantity in the receptacle, updating a total estimated volume of lost patient fluids 760, and updating a total estimated quantity of lost blood component 770. The method may include displaying some or all of the fluid-related information 780.

Collecting Fluids from the Patient

Collecting fluids from the patient into a receptacle 610 functions to accumulate a volume of lost patient fluids into the receptacle for evaluation. When collecting fluids ("fill" mode), the valve system may be adjusted to place the vacuum source, the receptacle, and a fluid retrieval device (or other fluid source) in fluidic communication. As a result, suction from the vacuum source may be routed throughout the system to draw fluids into the receptacle. For instance, as illustrated schematically in FIG. 8, collecting fluids 610 may include suctioning from a vacuum source through the third port of the receptacle to draw fluids through the inlet port into the receptacle.

Obtaining an Image

Obtaining an image of the collected fluids 630 functions to generate data which may be transformed into an estimate of blood volume and/or estimate of blood component concentration in the collected fluids. The image may include the entire receptacle or only a portion of the receptacle.

The image may be an optical image that is obtained with the aid of one or more features in the receptacle. For example, the image may capture a region of fluid having a substantially uniform thickness located between a fluid insert and a wall of the receptacle. As another example, the image may capture a region of fluid in which the fluid has a color gradient (e.g., due to a tapered surface of a fluid insert, walls of the receptacle, etc.).

In one variation, as shown in FIG. 6, an image of the collected fluids may be obtained upon detecting a high threshold volume of fluids in the receptacle 620 with a fluid level sensor. The high threshold volume may be correlated with the capacity of the receptacle, but need not be. In one example, upon reaching a high threshold volume of fluids in the receptacle, the method may include halting collection of fluid in the receptacle (e.g., by disabling suction to the fluid retrieval device), and waiting a predetermined period of time (e.g., five seconds) to permit receptacle contents to settle.

In another variation, an image of the fluids may be obtained periodically or based on detection of intermediate threshold volumes of fluids in the receptacle. For example, an image of the fluids may be obtained every two seconds or five seconds. As another example, an image of the fluids may be obtained every time a fluid level sensor detects that an additional 5 mL has been added to the receptacle. Any suitable time increment and/or volume increment may be used to trigger image capture.

Draining the Collected Fluids

Upon detecting a high threshold volume of fluids in the receptacle 620 and/or obtaining an image of the collected fluids 630, the method includes draining the collected fluids from the receptacle 640. When draining fluids ("flush" mode), the valve system may be adjusted to place the vacuum source and the outlet port in fluidic communication. As a result, suction from the vacuum source may be routed to draw fluids out of the receptacle. For instance, as illustrated schematically in FIG. 8, draining fluids 640 may include suctioning from the vacuum source through the outlet port to draw fluids through the outlet port and out of the receptacle.

To toggle from collecting fluids to draining fluids, the method may further include actuating a valve system. After being actuated to drain the collected fluids, the valve system may, at least in part, suspend fluidic communication between the vacuum source, the inlet port of the receptacle, and a fluid retrieval device (or other fluid source). Furthermore, after being actuated to drain the collected fluids, the valve system may open fluidic communication between the vacuum source and the outlet port of the receptacle. Additionally, actuating the valve system may involve opening the receptacle to ambient pressure, such as by actuating open a valve coupled to a fourth port of the receptacle.

In variations in which the valve system is automatically actuated, the method may include actuating the valve system based on a fluid level signal indicating a volume of fluids detected in the receptacle. Such actuation may involve, for example, activating an electromagnetic actuator such as a solenoid coupled to one or more valves. Alternatively, in variations in which the valve system is manually actuated, the method may include alerting a user to actuate the valve system.

Repeatedly Collecting and Draining

Figure 7:
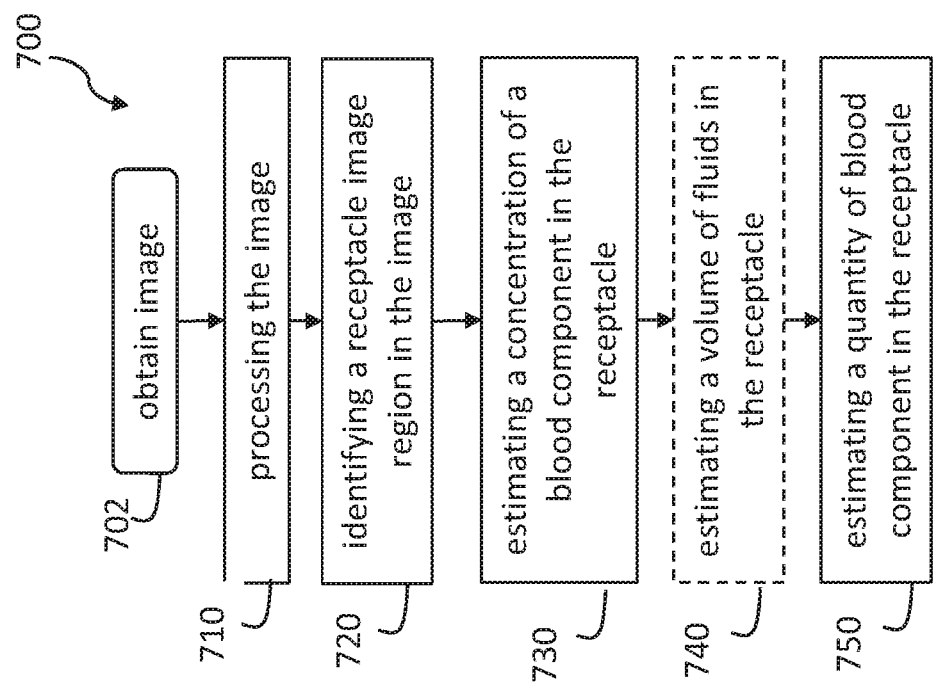
FIG. 7 is schematic of one variation of evaluating an image when assessing fluids from a patient.
Figure 8:
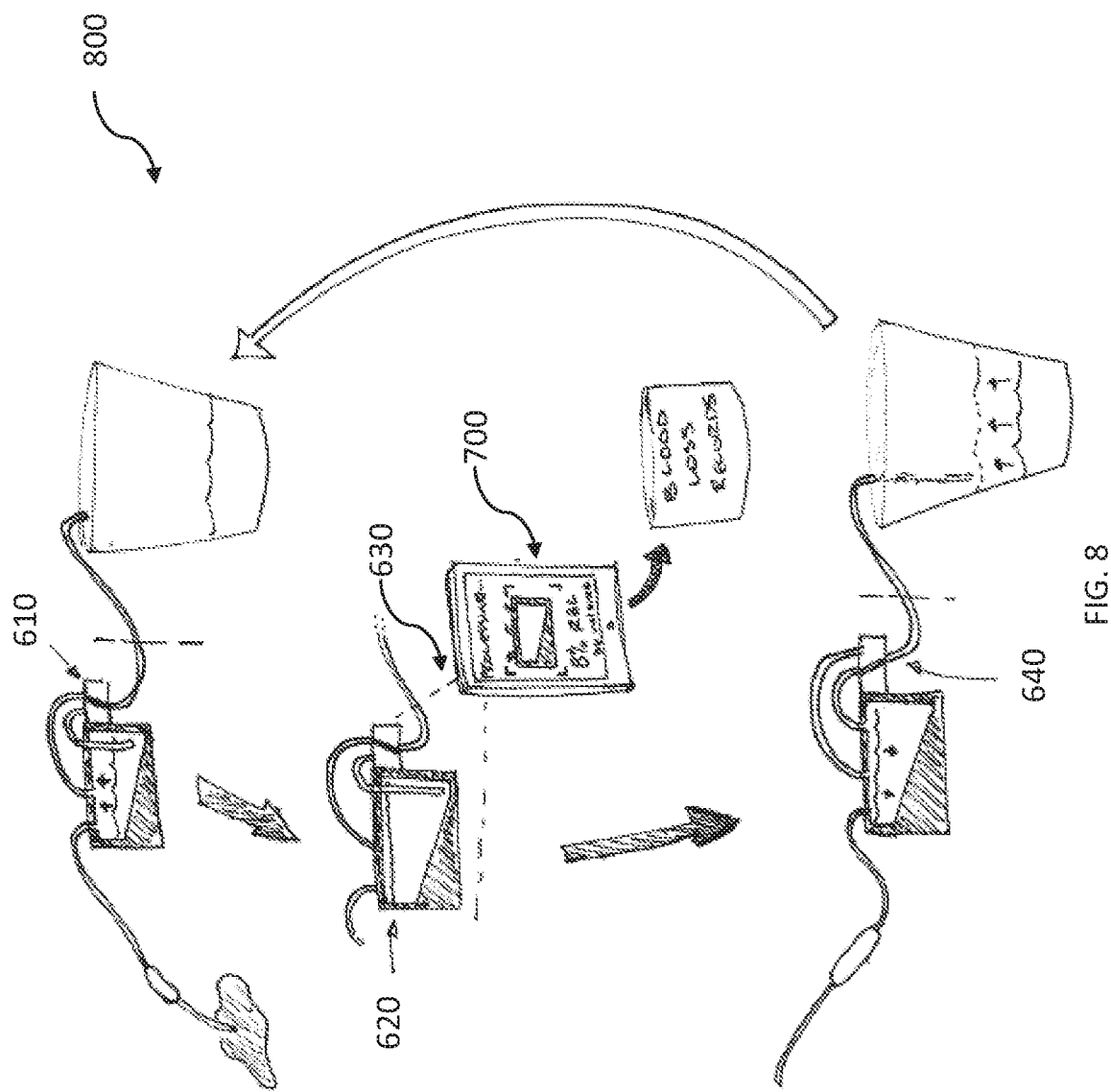
FIG. 8 is an illustrative schematic of one variation of a method for assessing fluids from a patient.

Upon detecting a low threshold volume of fluids in the receptacle 650 (or draining a sufficient amount of fluid from the receptacle), the method includes again collecting fluids from the patient in the receptacle 610. As shown in FIGS. 7 and 8, the above-described process may repeat in a cycle, until, for example, the surgical procedure is concluded and the patient is no longer losing fluids.

To toggle from draining fluids to collecting fluids, similar to toggling from collecting fluids to draining fluids, the method may further include actuating a valve system. After being actuated to collect more fluids, the valve system may, at least in part, restore fluidic communication between the vacuum source, the inlet port of the receptacle, and the fluid retrieval device (or other fluid source). Furthermore, after being actuated to collect more fluids, the valve system may suspend fluidic communication between the vacuum source and the outlet port of the receptacle. Additionally, actuating the valve system may involve closing the receptacle to ambient pressure, such as by actuating closed the valve coupled to the fourth port of the receptacle.

Evaluating the Image

The method may include evaluating each image. As shown in FIG. 7, after each image is obtained (702), evaluating the image 700 may include processing the image 710, identifying a receptacle image region in the image 720, estimating a concentration of a blood component in the receptacle 730, estimating a volume of fluids in the receptacle 740, and estimating a quantity of the blood component in the receptacle 750.

Processing

Processing the image may include normalizing the color characteristics of the image based on one or more optical fiducials (e.g., a color fiducial). Normalization may utilize the color fiducial to adjust for lighting conditions. For example, normalizing the image may include identifying a color fiducial captured in the image, determining an assigned color value associated with the identified color fiducial, and adjusting the image such that the color value of the color fiducial in the image substantially matches the assigned color value associated with the color fiducial. The assigned color value can, for example, be determined by looking up the color fiducial in a database (e.g., identified by code, position within a set of colored fiducial, position relative to a known feature of the receptacle, etc.). Adjustments to the image can include, for example, adjustment of exposure, contrast, saturation, temperature, tint, etc. Evaluating the image 700 may then proceed using the adjusted image.

Processing the image may additionally or alternatively include retrieving receptacle-related information associated with one or more optical fiducials and associating the image with the receptacle-related information. The optical fiducial may be scanned from the receptacle or manually entered into settings for the image analysis, and may be used to identify receptacle-related information. Retrieving receptacle-related information may be performed before, after, or during the obtaining of the image. Some or all of the receptacle-related information may be used when proceeding with evaluating the image 700.

Identifying a Receptacle Image Region

Identifying a receptacle image region 720 functions to identify a portion of the image whose pixel color values will be transformed into a blood component concentration. The receptacle image region may include the entire receptacle in the image, or only a portion of the receptacle corresponding to an identified volume of fluid. For example, the boundaries or outline of the receptacle image region may be detected using edge detection techniques, such as based on a pattern of pixels having biased red pixel color values (which suggests presence of blood) and other pixels without biased red pixel color values (which suggests absence of blood). As another example, the boundaries of the receptacle image region may be detected based on optical fiducials (e.g., coupled to the surface of the receptacle). In other examples, the boundaries of the receptacle image region may be detected using template matching techniques and/or other machine vision techniques. Once the receptacle image region is detected, all areas other than the receptacle image region may be cropped out or otherwise disregarded.

Estimating Blood Component Concentration and Quantity

Evaluation of the images may include estimating a blood component concentration 730. The blood component may be red blood cells (e.g., by volume) or hemoglobin, but may additionally or alternatively include other suitable components of blood. The estimation of blood component concentration may be based on various template matching techniques and/or parametric modeling techniques, as described below.

Template Matching and Parametric Modeling Techniques

For instance, to convert pixel color values in the receptacle image region to a blood component concentration, template matching techniques may include comparing a redness intensity of the receptacle image region against redness intensity from template images (e.g., a training set, samples analyzed previously). Each template image may be contained within a library of template images, and may be associated with a known blood, hemoglobin, red blood cell mass or volume, and/or other fluid characteristics. Generally, where the redness intensity of the receptacle image region is substantially similar to (and is paired with) a closest-matching template image, the receptacle image region may be estimated as depicting the same blood component concentration as the closest-matching template image.

In one example, K-nearest neighbor methods may be used for the template matching. More specifically, a K-nearest neighbor method may be used to compare the redness intensity of the receptacle image region with redness intensity values in the template images. Additionally or alternatively, a K-nearest neighbor method may be used to compare greenness intensity and/or a blueness intensity (e.g., in conjunction with a redness intensity) of pixels in the receptacle image region with greenness and/or blueness intensity values of the template images. Thus, the receptacle image region may be paired with the closest-matching template image identified with the K-nearest neighbor method, and the receptacle image region may be estimated as depicting the same blood component concentration associated with the closest-matching template image.

In another example, absolute differences in pixel intensities (e.g., in red, green, and/or blue intensities or color values) may be used for the template matching. Such an absolute difference in pixel intensities may be calculated at a wavelength of light that correlates with the blood component (e.g., at about 400 nm for estimating hemoglobin concentration). More specifically, a sum of absolute differences in pixel intensities may be used to compare pixel intensities between the receptacle image region and each template image. The closest-matching template image is identified when the sum of absolute differences is substantially minimal compared to other sums of absolute differences calculated for the receptacle image region and other template images. Thus, the receptacle image region may be paired with the closest-matching template image identified with the sum of absolute differences method, and the receptacle image region may be estimated as depicting the same blood component concentration associated with the closest-matching template image.

Additionally, parametric models may be used to convert pixel color values in the receptacle image region to a blood component concentration. Generally, color values of the template images may be used to train or generate a parametric model (mathematical function, curve, or algorithm etc.) that correlates a pixel color value to a blood component concentration. The parametric model may take an input of pixel intensities or color values (e.g., from the receptacle image region) and converted it into an output of estimated blood component concentration value.

Additionally or alternatively, the method may employ techniques such as those described in U.S. Pat. No. 8,792,693 filed Jul. 9, 2012 and entitled "SYSTEM AND METHOD FOR ESTIMATING EXTRACORPOREAL BLOOD VOLUME IN A PHYSICAL SAMPLE" and U.S. Pat. No. 8,983,167 filed Jan. 10, 2013 and entitled "SYSTEM AND METHOD FOR ESTIMATING A QUANTITY OF A BLOOD COMPONENT IN A FLUID CANISTER," each of which is hereby incorporated in its entirety by this reference. As another example, a parametric model similar to that depicted in FIG. 9 may be employed.

Variations

In one variation, the entire receptacle image region may be compared to a set of template images. The template images may capture exemplary receptacles containing different known concentrations of the blood component. When a particular template image is identified as a match (e.g., having pixel color values that are substantially similar to those in the receptacle image region), the fluid in the receptacle may be assumed to have a blood component concentration equal to the known blood component concentration associated with the matched template image.

In another variation, the receptacle image region may be divided in multiple subregions (i.e., pixel or pixel clusters), each of which may be compared to a set of template color values. Each template color value may be associated with a respective blood component concentration value or range of values. For instance, estimating the blood component concentration may include dividing the receptacle image region into multiple subregions (e.g., arranged in a grid), determining a representative pixel color value for each subregion (e.g., by averaging all pixel color values for each subregion), correlating each subregion with a blood component concentration value based on a comparison between the representative pixel color value and a set of template color values having associated blood component concentration values, and combining the blood component concentration values for the subregions to generate single composite blood component concentration representative of the receptacle image region (e.g., by averaging the subregion blood component concentration values). Another similar variation may use a parametric model, instead of template images, to correlate the representative pixel color value with a blood component concentration value for each subregion.

In another variation, in which the fluid in the receptacle has a color gradient (e.g., because the receptacle includes a slope), estimating the blood component concentration may involve matching the color gradient (i.e., distribution of pixel color values) in the receptacle image region with a set of template images of known blood component concentration. Similar to the variation described above, the template images may capture exemplary color gradients in fluid with known blood component concentrations.

In another variation, in which the fluid in the receptacle has a color gradient, estimating the blood component concentration may involve identifying the fluid volume thickness (as measured along the camera optical axis) corresponding to each subregion in the receptacle image region, determining a representative pixel color value for each subregion, applying a parametric model to each subregion to correlate the representative pixel color value and the fluid volume thickness for the subregion with a blood component concentration, and combining the blood component concentrations for the subregions into a single composite blood component concentration representative of the receptacle image region.

In yet another variation, the blood component concentration can generally be classified as high or low by comparing the redness intensity of at least some of the pixels in the receptacle image region with a threshold value. For example, blood component concentration may be classified as high if the redness intensity of pixels corresponding to the shallowest or thinnest region of fluid (as measured along the camera optical axis) in the receptacle exceeds a predetermined threshold. In contrast, blood component concentration may be classified as low if the redness intensity of pixels corresponding to the deepest or thickest region of fluid (as measured along the camera optical axis) in the receptacle less than a predetermined threshold. Furthermore, in another variations, the redness intensity at the shallowest/thinnest region or the deepest/thickest region of fluid (as measured along the camera optical axis) may be used as representative pixel color values for the entire receptacle image region and correlated to a blood component concentration based on template matching and/or parametric modeling techniques.

Estimating Volume of Fluids in the Receptacle

Evaluation of the images may include estimating a volume of fluids in the receptacle 740. For example, the size of a receptacle image region (which has been cropped to isolate biased red pixels) may be correlated to an estimated volume. Other edge detection techniques, template matching techniques, and/or parametric modeling techniques may be used to estimate fluid volume in the receptacle. Alternatively, in instances in which images are captured when fluid level sensors indicate the fluid volume in the receptacle has met a high threshold volume value, estimating a volume of fluids in the receptacle by evaluating the images may not be necessary, since the fluid volume may be assumed to be equal to the high threshold volume value.

Estimating Quantity of the Blood Component

Evaluation of the images may include estimating a quantity of the blood component in the receptacle 750. The quantity of blood component may be based on the estimated concentration of the blood component in the receptacle and the estimated volume of fluids in the receptacle. For example, the volume of the blood component may be estimated by multiplying values for the concentration of the blood component and the volume of fluids in the receptacle. Other quantitative metrics, such as mass or weight, may be derived from the estimated volume of the blood component.

Updating Database

The method may include updating a total estimated volume of lost patient fluids 760, by summing the previous intermittent estimated volumes of fluids that have filled and drained from the receptacle. Similarly, the method may include updating a total estimated volume of lost blood component 770 by summing the previous intermittent estimated quantities of blood component lost by the patient. The updated total estimates may, for example, be stored in local memory on a handheld or mobile device or other computing device, communicated to a server or database for remote storage, etc. The update may occur during the surgical procedure (e.g., after each time a volume of fluids is estimated, or periodically such as every five seconds) to provide an estimate of cumulative or total blood loss and/or of cumulative or total blood component loss. Additionally or alternatively, the update may occur at the conclusion of the surgical procedure. For example, as shown in FIG. 8, after evaluating the image 700, one or more of the updated estimates may be communicated by a processor to a database (e.g., for medical records, hospital administration purposes, etc.), such as by a wired or a wireless connection.

Displaying

The method may include displaying some or all of the fluid-related information 780 (e.g., total estimated volume of lost patient fluids, total estimated quantity of lost blood component, etc.) on a display such as a monitor. The display may reflect, on a substantially real-time basis, the estimated metrics as they are updated throughout and/or after the surgical procedure. Additionally, the method may include displaying some or all of the images of the receptacle/fluid as they are captured, alerts to the user (e.g., when estimated total volume of lost patient fluids or total estimated quantity of lost blood component exceeds a threshold) and/or other suitable information.

Other Variations

Figure 9:
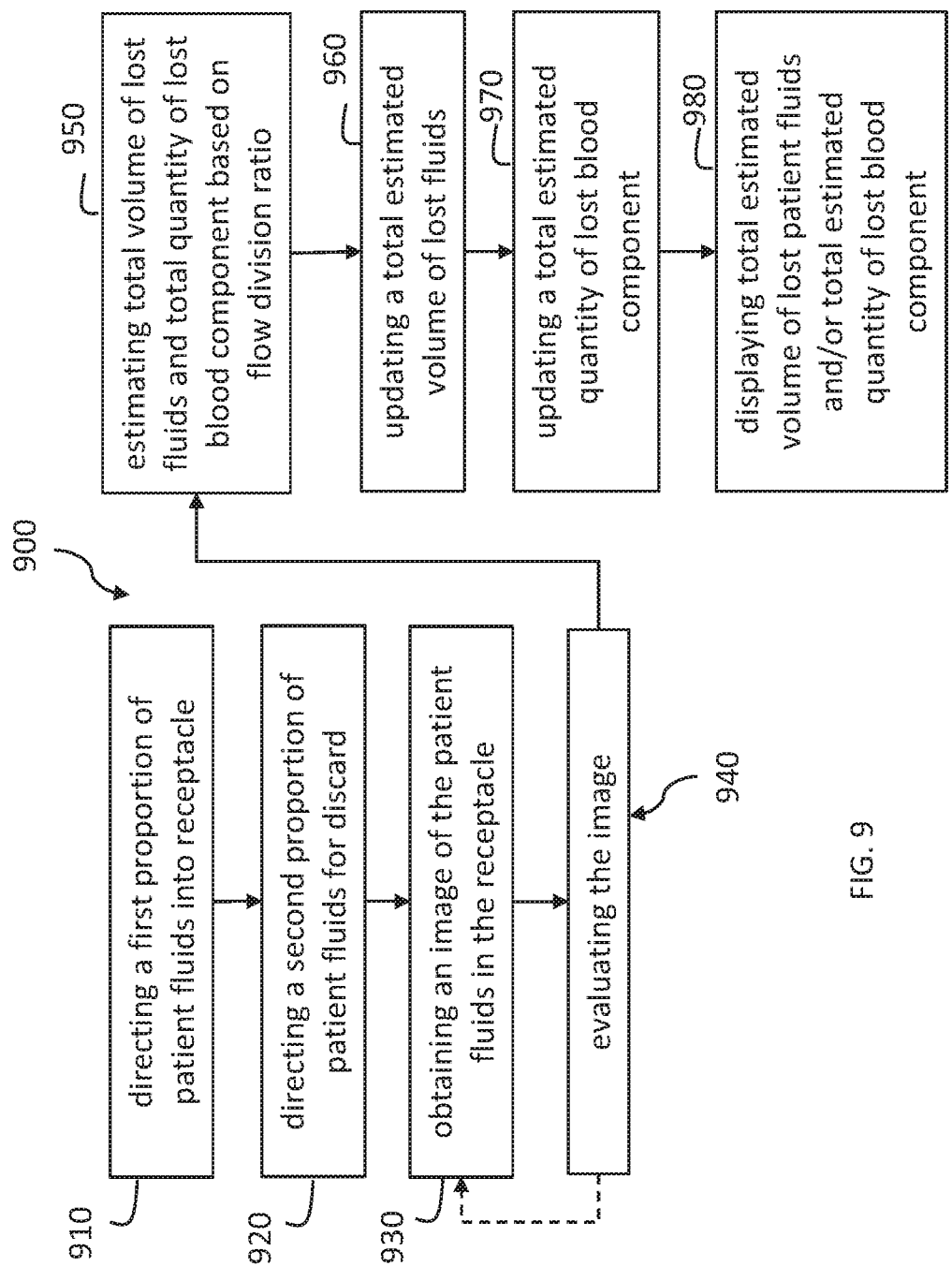
FIGS. 9 and 10 are schematics of a variation of a method using a flow divider for assessing fluids from a patient.

As shown in FIG. 9, a method 900 for assessing fluids uses a flow divider system as described above with reference to FIG. 5. The method 900 may include: directing a first proportion of patient fluids into a receptacle (e.g., with a flow divider), directing a second proportion of patient fluids for discard (e.g., to a second receptacle) 920 in which the second proportion is greater than the first proportion according to a flow division ratio, and obtaining one or more images of the patient fluids in the receptacle 930. For each image obtained, the method 900 may include evaluating the image 940 to estimate fluid volume and a blood component quantity in the receptacle, and estimating total volume of lost fluids and total quantity of lost blood component 950 based on flow division ratio. Additionally, the method 900 may include updating a total estimated volume of lost patient fluids 960, and updating a total estimated quantity of lost blood component 970. The method may include displaying some or all of the fluid-related information 980.

Portions of method 900 may be substantially similar to similarly-named processes of method 600 described above. For example, evaluating the image 940 may be substantially similar to evaluating the image 700. However, estimating total volume of lost fluids (Vblood, tot) and total quantity of lost blood component 950 (QBC, tot) may be particular to methods using a flow divider system. Since the patient fluid in the receptacle is a representative sample of all patient fluid collected, assessments of patient fluid in the receptacle may be projected or extended to provide assessments of the total patient fluid collected by the fluid retrieval device (or from another fluid source). More specifically, the method may include estimating fluid volume that was discarded ($V_{Blood,\ discard}$) by multiplying the flow division ratio and the estimated fluid volume in the receptacle ($V_{Blood,\ rec}$). Similarly, the method may include estimating blood component quantity that was discarded ($Q_{BC,\ discard}$) by multiplying the flow division ratio and the estimated blood component quantity in the receptacle ($Q_{BC,\ rec}$). Finally, total volume of lost fluids ($V_{mood,\ tot}$) can be estimated as the sum of estimated fluid volume in the receptacle and estimated fluid volume that was discarded. Similarly, total quantity of lost blood component ($Q_{BC,\ tot}$) can be estimated as the sum of estimated blood component in the receptacle and estimated fluid volume that was discarded. This estimation may be summarized as:

$$V_{Blood,tot} = V_{Blood,rec} + V_{Blood,discard} = V_{Blood,rec} + (\text{ratio})(V_{mood,rec}) \quad (1)$$

$$Q_{BC,tot} = Q_{BC,rec} + Q_{BC,discard} = Q_{BC,rec} + (\text{ratio})(Q_{BC,rec}) \quad (2)$$

Figure 10:
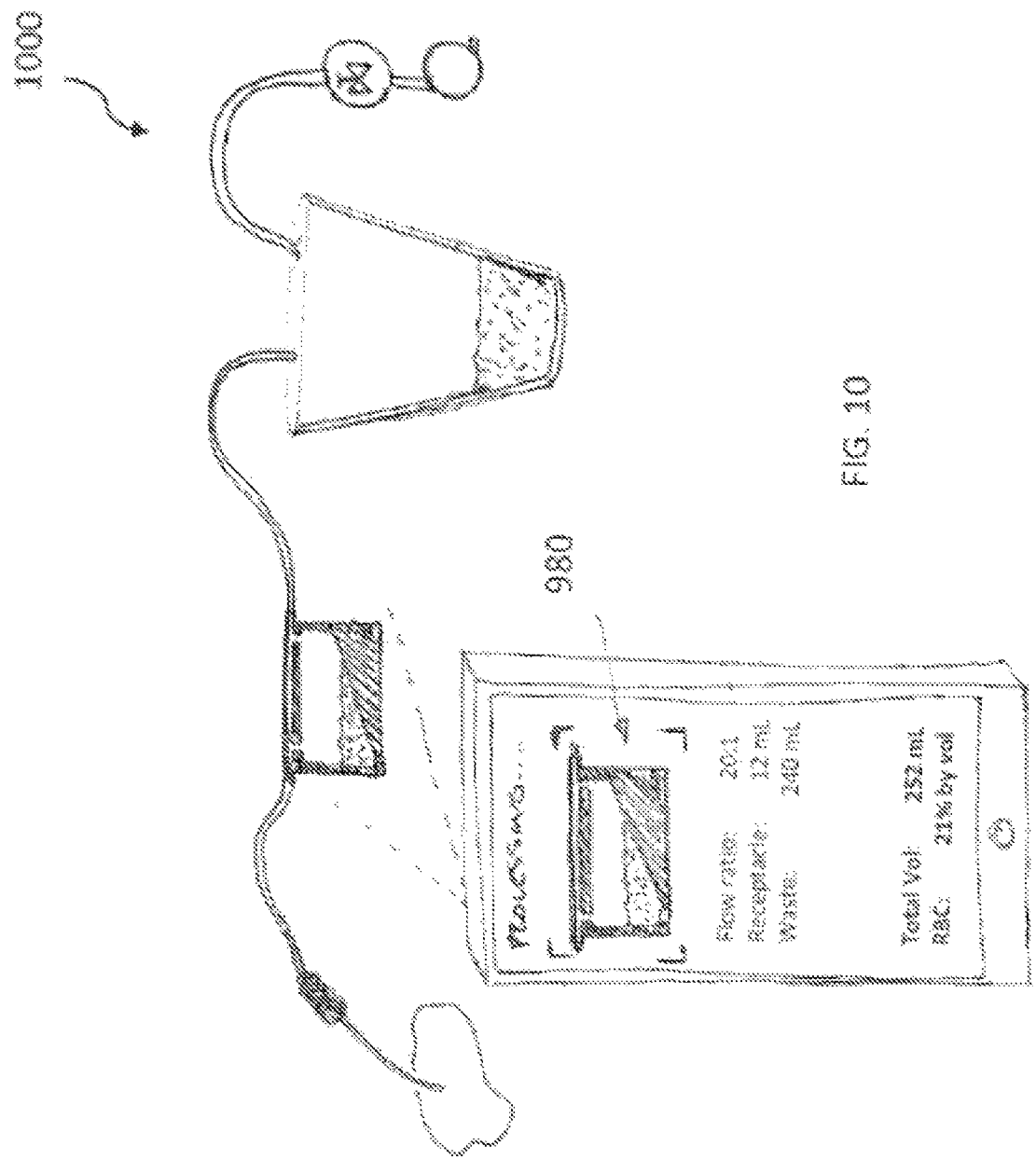

An example of estimating total volume of lost fluids ($V_{mood,\ tot}$), is illustrated schematically in the method 1000 in FIG. 10, which shows a flow divider system with an exemplary flow division ratio meaning that for every twenty given parts of incoming fluid that are diverted for discard, one part of incoming fluid is directed into the receptacle. For example, if the estimated fluid volume in the receptacle is about 12 mL, then in accordance with Equation 1, multiplying the 20:1 flow division ratio and the estimated fluid volume in the receptacle yields an estimate of about 240 mL of fluid that was discarded. In accordance with Equation 2, the total volume of lost fluids is the sum of the estimated fluid volume in the receptacle and estimated fluid volume that was discarded, or about 252 mL. As shown in FIG. 10, some or all of this fluid-related information may be displayed on a display (e.g., handheld or mobile device) (980).

IV. Kits

A kit may include any pail of the systems described herein. In further aspects, a kit may additionally or alternatively include a tangible non-transitory computer readable medium having computer-executable (readable) program code embedded thereon that may provide instructions for causing one or more processors, when executing the instructions, to perform one or more of the methods for assessing fluids from a patient as described herein. The kit may include instructions for use of at least some of its components, including but not limited to: instructions for installation, use, and/or care of the receptacle, instructions for installing the computer-executable (readable) program code with instructions embedded thereon, etc.

As a person skilled in the art will recognize from the previous detailed description and from the figures and claims, modifications and changes can be made to the described and illustrated embodiments without departing from the scope of the invention. Furthermore, different variations of the methods and systems include various combinations and permutations of the steps and other elements described herein.

The invention claimed is:

1. A method comprising:
   directing suction from a vacuum source to suction a flow of fluids from a patient and into a receptacle;

determining with a processor that the receptacle is filled to a high threshold fluid volume;
actuating a valve, or disabling the suction to permit the fluids in the receptacle to settle;
thereafter, triggering a camera to capture an image based on the receptacle being filled to the high threshold fluid volume, wherein the image depicts the fluids within the receptacle;
evaluating the image to determine an estimated blood component concentration in the fluids;
determining an intermittent estimate of blood loss based on the estimated blood component concentration and the high threshold fluid volume;
updating a total estimate of blood loss based on the intermittent estimate of blood loss; and
displaying on a display the total estimate of blood loss.

2. The method of claim 1, further comprising triggering the camera to capture additional images based on the receptacle being filled to intermediate fluid volumes less than the high threshold fluid volume.

3. The method of claim 1, further comprising draining the fluids from the receptacle based on the receptacle being filled to the high threshold fluid volume, wherein the filling and draining of the fluids is cyclically performed while the camera intermittently captures the image and additional images of the receptacle.

4. The method of claim 1, further comprising, in response to the receptacle being filled to the high threshold fluid volume and after the image is captured, actuating a valve to facilitate draining of the fluid through an outlet port of the receptacle.

5. The method of claim 4, further comprising:
determining with a processor that the receptacle is filled to a low threshold fluid volume; and
actuating the valve to facilitate filling of the receptacle.

6. A method comprising:
directing suction from a vacuum source to suction a flow of fluids from a patient and into a receptacle;
periodically capturing a set of images with a camera, wherein each image of the set of images depicts the fluids within the receptacle;
analyzing the set of images to detect a fluid level of the fluids within the receptacle and to generate a fluid level signal based on the detected fluid level;
determining that the fluid level signal exceeds a predefined volume increment;
actuating a valve, or disabling the suction to permit the fluids in the receptacle to settle;
thereafter, triggering the camera to capture another image in response to the fluid level signal;
analyzing the another image to determine an estimated blood component concentration in the fluids;
determining a total estimate of blood loss based on the fluid level signal and the estimated blood component quantity in the fluid; and
displaying on a display the total estimate of blood loss.

7. The method of claim 6, wherein the step of periodically capturing the images with the camera is performed at fixed timing increments.

8. The method of claim 6, further comprising analyzing the first set of images to determine intermittent estimated blood component concentrations in the fluids.

9. The method of claim 8, further comprising estimating intermittent estimates of blood loss based on the estimated intermittent blood component concentrations and corresponding intermittent volumes of fluids within the receptacle.

10. The method of claim 8, further comprising displaying on the display the estimating intermittent estimates of blood loss.

11. The method of claim 6, further comprising, in response to the receptacle being filled to the high threshold fluid volume and after the another image is captured, actuating a valve to facilitate draining of the fluid through an outlet port of the receptacle.

12. The method of claim 11, further comprising:
determining with a processor that the receptacle is filled to a low threshold fluid volume; and
actuating the valve to facilitate filling of the receptacle.

13. A method comprising:
directing suction from a vacuum source to suction a flow of fluids from a patient and into a receptacle;
determining with a processor that the receptacle is filled to a first intermediate fluid volume;
triggering a camera to capture a first image based on the receptacle being filled to the first intermediate fluid volume;
determining with a processor that the receptacle is filled to a second intermediate fluid volume;
triggering the camera to capture a second image based on the receptacle being filled to the second intermediate fluid volume;
determining with a processor that the receptacle is filled to a high threshold fluid volume;
triggering the camera to capture a third image based on the receptacle being filled to the high threshold fluid volume, wherein the image depicts the fluids within the receptacle;
evaluating the third image to determine an estimated blood component concentration in the fluids;
determining an estimate of blood loss based on the estimated blood component concentration and the high threshold fluid volume;
updating a total estimate of blood loss based on the estimate of blood loss; and
displaying on a display the total estimate of blood loss.

14. The method of claim 13, further comprising evaluating at least one of the first image and the second image to determine at least one intermittent estimated blood component concentration in the fluids.

15. The method of claim 14, further comprising estimating at least one intermittent estimate of blood loss based on the at least one estimated intermittent blood component concentrations and corresponding intermediate volumes of fluids within the receptacle.

16. The method of claim 15, further comprising displaying on the display the at least one intermittent estimate of blood loss.

17. The method of claim 13, further comprising, in response to the receptacle being filled to the high threshold fluid volume and after the third image is captured, actuating a valve to facilitate draining of the fluid through an outlet port of the receptacle.

18. The method of claim 17, further comprising:
determining with a processor that the receptacle is filled to a low threshold fluid volume; and
actuating the valve to facilitate filling of the receptacle.

* * * * *